(12) United States Patent
Shimomura et al.

(10) Patent No.: US 12,268,821 B2
(45) Date of Patent: Apr. 8, 2025

(54) AWAKENING INDUCING DEVICE AND AWAKENING INDUCING SYSTEM

(71) Applicant: Panasonic Intellectual Property Management Co., Ltd., Osaka (JP)

(72) Inventors: Yoshihiro Shimomura, Chiba (JP); Risa Fujita, Chiba (JP); Yali Xia, Chiba (JP); Daisuke Wakuda, Kyoto (JP); Shinichi Shikii, Nara (JP); Aki Yoneda, Hyogo (JP)

(73) Assignee: PANASONIC AUTOMOTIVE SYSTEMS CO., LTD., Kanagawa (JP)

( * ) Notice: Subject to any disclaimer, the term of this patent is extended or adjusted under 35 U.S.C. 154(b) by 281 days.

(21) Appl. No.: 17/784,983

(22) PCT Filed: Dec. 10, 2020

(86) PCT No.: PCT/JP2020/046045
§ 371 (c)(1),
(2) Date: Jun. 13, 2022

(87) PCT Pub. No.: WO2021/125043
PCT Pub. Date: Jun. 24, 2021

(65) Prior Publication Data
US 2023/0016979 A1   Jan. 19, 2023

(30) Foreign Application Priority Data
Dec. 17, 2019 (JP) .................. 2019-227068

(51) Int. Cl.
*B60N 2/90* (2018.01)
*A61M 21/00* (2006.01)

(52) U.S. Cl.
CPC .............. *A61M 21/00* (2013.01); *B60N 2/90* (2018.02); *A61M 2021/0022* (2013.01);
(Continued)

(58) Field of Classification Search
CPC ............ B60N 2002/981; A61M 21/00; A61M 2021/0022; A61M 2021/0083; A61M 2210/086
See application file for complete search history.

(56) References Cited

U.S. PATENT DOCUMENTS

2006/0255920 A1* 11/2006 Maeda ............... B60N 2/02246
340/407.1
2010/0327673 A1* 12/2010 Jun ......................... H02K 33/16
310/25
(Continued)

FOREIGN PATENT DOCUMENTS

JP      2001-199296      7/2001
JP      2004-246791      9/2004
(Continued)

OTHER PUBLICATIONS

Official communication in corresponding Japanese application No. JP2021-565532 dated Dec. 5, 2023, along with English translation.
(Continued)

*Primary Examiner* — Kenneth J Malkowski
(74) *Attorney, Agent, or Firm* — GREENBLUM & BERNSTEIN, P.L.C.

(57) ABSTRACT

An awakening inducing device induces a vibration device disposed in a seat at a position where the vibration device opposes at least one of a muscle belly portion or an insertion portion of a hamstring of a user sitting on the seat; and a control device that, by controlling the vibration device, causes the vibration device to given vibration stimulation to at least one of the muscle belly portion or the insertion portion.

11 Claims, 10 Drawing Sheets

(52) U.S. Cl.
CPC ............... *A61M 2021/0083* (2013.01); *A61M 2210/0606* (2013.01); *A61M 2210/086* (2013.01); *A61M 2230/005* (2013.01); *B60N 2002/981* (2018.02)

(56) References Cited

U.S. PATENT DOCUMENTS

| | | | | |
|---|---|---|---|---|
| 2011/0018740 | A1* | 1/2011 | Boren | B60N 2/976 340/965 |
| 2012/0158252 | A1* | 6/2012 | Bonarens | B60N 3/06 701/49 |
| 2018/0037236 | A1 | 2/2018 | Yamaguchi | |
| 2018/0170228 | A1* | 6/2018 | Kono | B06B 1/045 |
| 2019/0167941 | A1* | 6/2019 | Yamaguchi | G08G 1/16 |

FOREIGN PATENT DOCUMENTS

| | | |
|---|---|---|
| JP | 2006-341839 | 12/2006 |
| JP | 2016-153969 | 8/2016 |
| JP | 2018-023664 | 2/2018 |

OTHER PUBLICATIONS

Gordon et al., "1988 Anthropometric Survey of U.S. Army Personnel: Summary Statistics Interim Report", Anthropology Research Project, Inc., Yellow Springs, Ohio, 45387, Mar. 1989.

Naito, "Body Representation in the Brain for Motor Control and Body Cognition", Conference of the Japanese Society of Neurological Physical Therapy, Physical Therapy Japan, vol. 43, Suppl. No. 3, 2016, pp. 59-62, along with partial English translation thereof.

Official Communication issued in International Patent Application No. PCT/JP2020/046045, dated Jan. 19, 2021, along with an English translation thereof.

Official Action issued in Japanese patent application JP 2021-565532 dated Sep. 12, 2023, along with English translation thereof.

* cited by examiner

AWAKENING INDUCING DEVICE AND AWAKENING INDUCING SYSTEM

TECHNICAL FIELD

The present disclosure relates to an awakening inducing device and an awakening inducing system.

BACKGROUND ART

Conventionally, there are devices that awaken a user by giving vibration stimulation to a specific area on the user (see, for example, Patent Literature (PTL) 1).

PTL 1 discloses a device that awakens a user effectively by giving vibration stimulation to the tendon portion of the user's latissimus dorsi muscle or the tendon portion of the user's gluteus medius muscle.

CITATION LIST

Patent Literature

[PTL 1]

Japanese Unexamined Patent Application Publication No. 2016-153969

Non Patent Literature

[NPL 1]

Gordon, Claire C. et al. "1988 Anthropometric Survey of U.S. Army Personnel: Summary Statistics" Interim Report. March, 1989.

SUMMARY OF INVENTION

Technical Problem

Devices that awaken users are desired to awaken the users more clearly, that is, to awaken the users fully.

The present disclosure provides an awakening inducing device and so on that can awaken a user more fully than conventional awakening inducing devices.

Solution to Problem

To address the problem described above, an awakening inducing device according to one aspect of the present disclosure includes: a vibration device disposed in a seat at a position where the vibration device opposes at least one of a muscle belly portion or an insertion portion of a hamstring of a user sitting on the seat; and a control device that, by controlling the vibration device, causes the vibration device to give vibration stimulation to the at least one of the muscle belly portion or the insertion portion.

In addition, an awakening inducing system according to one aspect of the present disclosure includes: the awakening inducing device described above; the seat; a state detecting sensor that detects state information indicating a state of the user sitting on the seat; and a determining device that determines a degree of drowsiness of the user based on the state information detected by the state detecting sensor, wherein the control device controls the vibration device based on a determination result of the determining device.

Advantageous Effects of Invention

The awakening inducing device and so on according to some aspects of the present disclosure can awaken a user more fully than conventional techniques.

DESCRIPTION OF EMBODIMENTS

Overview of the Present Disclosure

Figure 1:
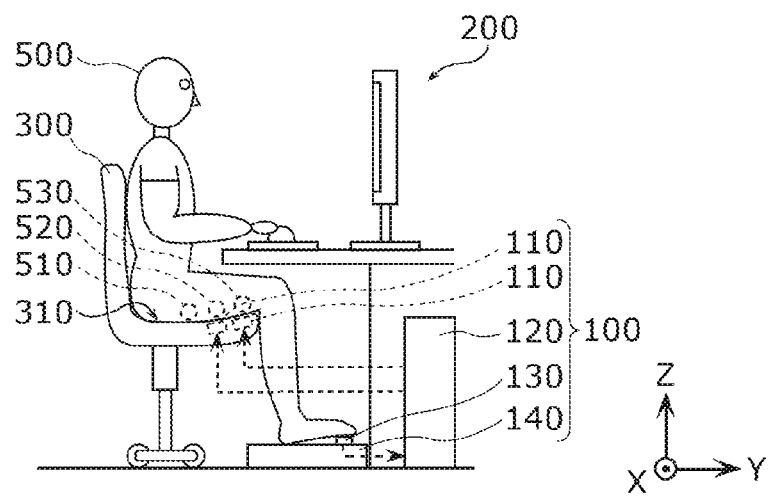
FIG. 1 is a side view illustrating an awakening inducing system according to Embodiment 1.

To increase the drowsiness eliminating effect, that is, to awaken a user fully, the nerve activity level of the supplementary motor area of the user may be increased. The supplementary motor area is known not to be activated by vibration stimulation that causes no motion illusion but to be activated by vibration stimulation that causes a motion illusion. In other words, giving a user vibration stimulation that causes a clear motion illusion can activate the supplementary motor area of the user, that is, can increase the nerve activity level of the supplementary motor area of the user. Furthermore, activating the supplementary motor area can lead to increased stimulation to, for example, the reticular formation (the brainstem reticular formation). Stimulating the reticular formation awakens the user. In other words, giving a user vibration stimulation that causes a clear motion illusion can awaken the user effectively.

Through diligent study, the inventors of the present application have found that giving vibration stimulation to a specific area on a user can produce a more intense illusion (motion illusion). In other words, the inventors have found that giving vibration stimulation to a specific area on a user makes it possible to awaken the user more fully than conventional techniques.

An awakening inducing device according to one aspect of the present disclosure includes a vibration device and a control device. The vibration device is disposed in a seat at a position where the vibration device opposes at least one of a muscle belly portion or an insertion portion of a hamstring of a user sitting on the seat. The control device, by controlling the vibration device, causes the vibration device to give vibration stimulation to at least one of the muscle belly portion or the insertion portion.

This configuration makes it possible to give vibration stimulation to at least one of the muscle belly portion or the insertion portion of the user. After diligent study, the inventors of the present application have found that it is possible to awaken the user more fully than conventional techniques by giving vibration stimulation to at least one of the muscle belly portion or the insertion portion of the user. In other words, the awakening inducing device according to one aspect of the present disclosure can awaken the user more fully than conventional techniques by giving vibration stimulation to at least one of the muscle belly portion or the insertion portion of the user.

For example, the vibration device is disposed in the seat at a position where the vibration device opposes the insertion portion, and the control device causes the vibration device to give the vibration stimulation to the insertion portion.

This configuration makes it possible to give vibration stimulation to the insertion portion of the user. After diligent study, the inventors of the present application have found that it is possible to awaken the user more effectively by giving vibration stimulation to particularly the insertion portion, of the muscle belly portion and the insertion portion, of the user. In other words, such a configuration makes it possible to awaken the user more effectively by giving vibration stimulation to the insertion portion of the user.

For example, the awakening inducing device according to one aspect of the present disclosure further includes a footrest that receives at least one foot of the user, and the footrest is disposed at a position where, when the user sitting on the seat has placed a foot on the footrest, at least one of the muscle belly portion or the insertion portion is in contact with the seat.

With this configuration, when the footrest is disposed at an appropriate position and when the user has placed one or both of his or her feet on the footrest, the user can be brought into a posture that allows the vibration device to give vibration stimulation appropriately to at least one of the muscle belly portion or the insertion portion. Hence, this configuration makes it possible to give vibration stimulation appropriately to at least one of the muscle belly portion or the insertion portion of the user.

For example, the awakening inducing device according to one aspect of the present disclosure further includes a receiving device that receives an instruction. The receiving device is disposed on the footrest, and the control device performs at least one of starting or stopping control that causes the vibration device to give the vibration stimulation, based on the instruction received by the receiving device.

This configuration can help prevent a situation in which vibration stimulation is given to the user at a timing that is not intended by the user. For example, if the user is given vibration stimulation at a timing that is not intended by the user while the user is driving, this vibration stimulation may startle the user, causing dangerous driving. As such, the user selects, via the receiving device, the timing at which the user is given vibration stimulation as desired, and this can keep the user from being startled by vibration stimulation given at an unintended timing.

For example, the seat is a driver's seat of a vehicle, and the footrest is disposed at a position where the user sitting in the driver's seat places a left foot.

For example, the seat is a driver's seat of a vehicle, and the vibration device is disposed at a position where the vibration device opposes, of two legs of the user, only a left leg of the user sitting in the driver's seat.

If the user is startled by vibration stimulation while driving or if vibration stimulation is undesirable and unpleasant to the user, this may cause the user to unintentionally move the leg to which the vibration stimulation has been given. The driving action of stepping on the accelerator or the brake is often carried out with the right foot. Therefore, giving vibration stimulation to the left leg can prevent a situation in which the driving of the user is impeded, even if the user has unintentionally moved the leg to which the vibration stimulation has been given. As the footrest is disposed at the position where the left foot is placed, when the user has placed the left foot on the footrest, the user can be brought into a posture that allows the vibration device to give vibration stimulation appropriately to at least one of the muscle belly portion or the insertion portion of the left leg.

For example, the vibration device includes an eccentric motor, a rotary motor with a cam mechanism, or a voice coil motor, and the vibration device is disposed in the seat with a vibration direction of the vibration device extending in a vertical direction.

With this configuration, the control device can cause the vibration device to give vibration stimulation to the user more effectively by causing the vibration device to vibrate in the vertical direction with a simple configuration.

For example, the eccentric motor, the rotary motor with a cam mechanism, or the voice coil motor is disposed within 40 cm from a front end of the seat.

With this configuration, the control device can, by controlling the vibration device, cause the vibration device to give vibration stimulation appropriately to at least one of the muscle belly portion or the insertion portion.

An awakening inducing system according to one aspect of the present disclosure includes the awakening inducing device described above, the seat, a state detecting sensor that detects state information indicating a state of the user sitting on the seat, and a determining device that determines a degree of drowsiness of the user based on the state information detected by the state detecting sensor. The control device controls the vibration device based on a determination result of the determining device.

With this configuration, when it is determined that the user needs to be awakened based on the degree of drowsiness of the user, the user can be awakened by being given vibration stimulation to at least one of the muscle belly portion or the insertion portion of the user appropriately.

Hereinafter, some embodiments of the present disclosure will be described with reference to the drawings. The embodiments described below merely illustrate general or specific examples of the present disclosure. Hence, the numerical values, the constituent elements, the arrangement positions and the connection modes of the constituent elements, the processes (the steps), the order of the processes, and so on illustrated in the following embodiments are examples and are not intended to limit the present disclosure.

Moreover, the drawings are schematic diagrams and do not necessarily provide the exact depictions. Hence, the scales and so on do not necessarily match among the drawings. In the drawings, substantially identical components are given identical reference characters, and duplicate descriptions thereof may be omitted or simplified.

In the present specification and the drawings, the X-axis, the Y-axis, and the Z-axis represent the three axes of a three-dimensional orthogonal coordinate system. In the following embodiments, the Z-axis direction is the vertical direction, and the direction perpendicular to the Z-axis (the direction parallel to the XY-plane) is the horizontal direction. In addition, the positive direction along the Z-axis is the vertically upward direction.

Embodiment 1

[Configuration]

First, a configuration of an awakening inducing system that includes an awakening inducing device according to Embodiment 1 will be described.

Figure 2:
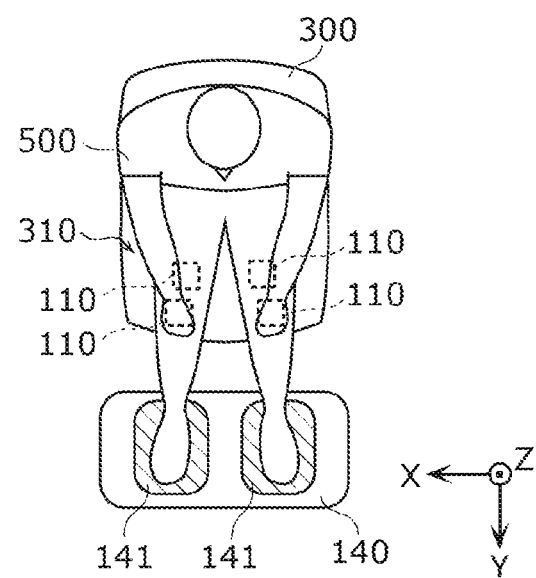
FIG. 2 is a top view for describing a positional relationship between vibration devices according to Embodiment 1 and a user.
Figure 3:
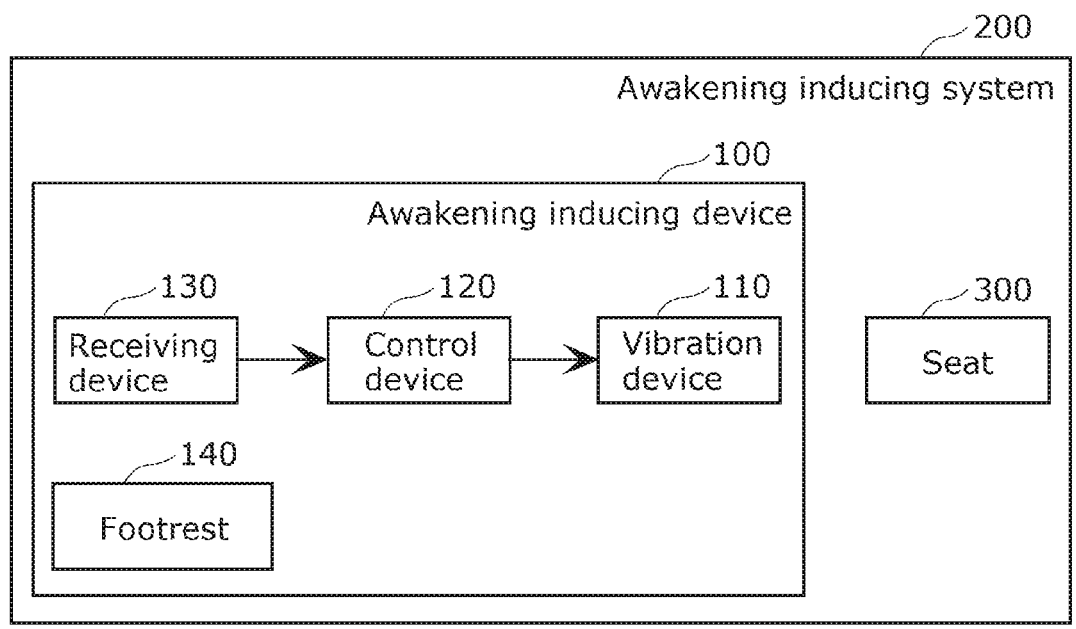
FIG. 3 is a block diagram illustrating a functional configuration of the awakening inducing system according to Embodiment 1.
Figure 4:
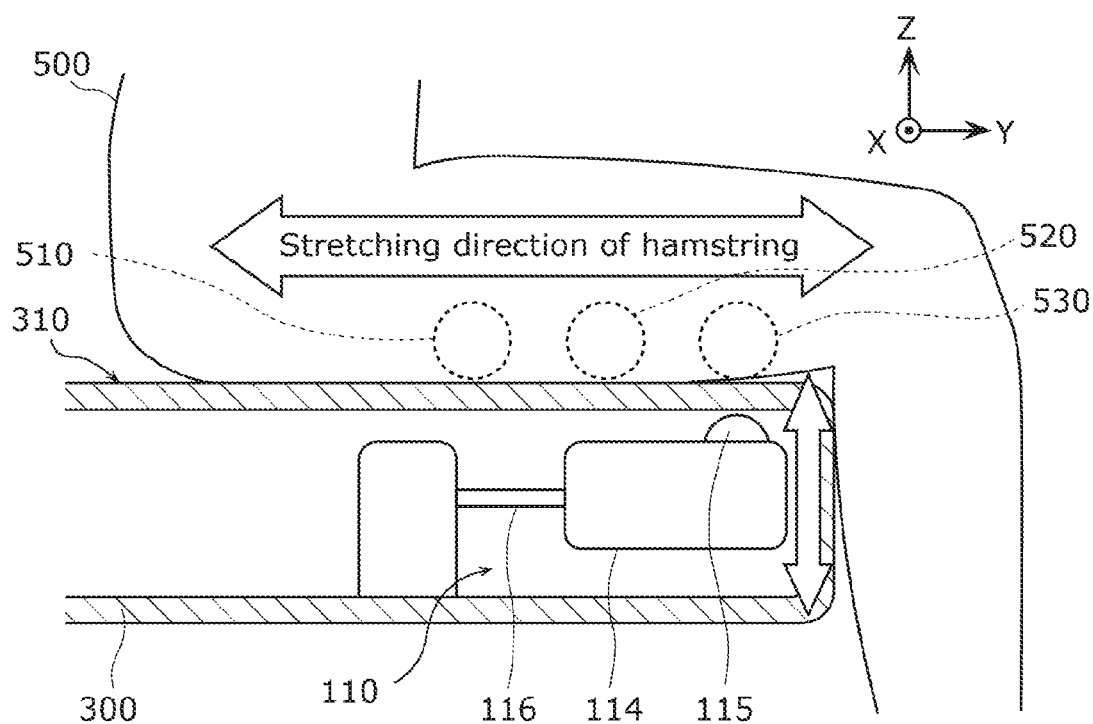
FIG. 4 is an illustration for describing a position on a user to which the vibration devices according to Embodiment 1 give vibration stimulation.
Figure 5:
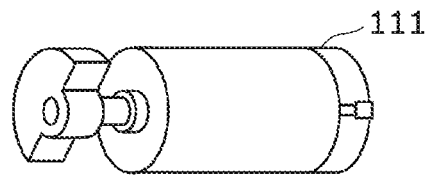
FIG. 5 is a diagram illustrating an example of an eccentric motor.

FIG. 1 is a side view illustrating awakening inducing system 200 according to Embodiment 1. FIG. 2 is a top view for describing a positional relationship between vibration devices 110 according to Embodiment 1 and user 500. FIG. 3 is a block diagram illustrating a functional configuration of awakening inducing system 200 according to Embodiment 1. FIG. 4 is an illustration for describing a position on user 500 to which vibration devices 110 according to Embodiment 1 give vibration stimulation. FIG. 4 illustrates only a portion of the inside of seat 300 for description. FIG. 5 is a diagram illustrating an example of eccentric motor 111 included in each vibration device 110. FIG. 1 and FIG. 2 each show a plurality of vibration devices 110, whereas FIG. 3 and FIG. 4 each show only one vibration device 110 for description. There is no particular limitation on the number of vibration devices 110 to be included in awakening inducing device 100.

Awakening inducing system 200 is a system that awakens user 500 by giving vibration stimulation to at least one of muscle belly portion 520 or insertion portion 530 of one or each of the hamstrings of user 500 sitting on seat 300 disposed in a mobile body, such as an automobile, or in an office.

Awakening inducing system 200 induces awakening in user 500 by giving vibration stimulation to user 500 who is experiencing a decrease in efficiency or facing a possible safety concern due to drowsiness while, for example, working at a desk, studying, or driving.

Awakening inducing system 200 includes awakening inducing device 100 and seat 300.

Awakening inducing device 100 is a device that awakens user 500 by giving vibration stimulation to at least one of muscle belly portion 520 or insertion portion 530 of one or each of the hamstrings of user 500 sitting on seat 300 disposed in a mobile body, such as an automobile, or in an office. In this example, awakening user 500 means at least one of bringing the state of user 500 to the one in which user 500 is more awake than in the current state or maintaining the awake state of user 500. In other words, awakening user 500 can mean eliminating drowsiness of user 500 (i.e., lowering the degree of drowsiness (the level of drowsiness)) or keeping user 500 from becoming drowsy (i.e., keeping the degree of drowsiness from rising). In the following description, either case is simply expressed as awakening user 500.

There is no particular limitation on the shape of seat 300 as long as seat 300 includes seating surface 310 on which user 500 sits. Seating surface 310 may be made of a material that can be deformed (elastically deformed) by vibration devices 110. Seating surface 310 is formed, for example, of a cushiony material.

Awakening inducing device 100 includes vibration devices 110, control device 120, receiving device 130, and footrest 140. Control device 120 is connected to each vibration device 110 and receiving device 130 such that these connected devices can transmit or receive signals therebetween via a wired circuit or a wireless circuit.

Vibration devices 110 are each a device that vibrates to give vibration stimulation to at least one of muscle belly portion 520 or insertion portion 530. Each vibration device 110 is disposed in seat 300 at a position where vibration device 110 opposes at least one of muscle belly portion 520 or insertion portion 530 of a hamstring of user 500 sitting on seat 300. According to the present embodiment, vibration devices 110 are disposed inside seat 300 and disposed at respective positions where vibration devices 110 can give vibration stimulation to user 500 via seating surface 310. In other words, vibration devices 110 are provided in seat 300 at respective positions where vibration devices 110 oppose user 500 via seating surface 310.

A hamstring is a collective term for a lower limb posterior thigh muscle and includes a biceps femoris, a semimembranosus, and a semitendinosus. A hamstring is divided into origin portion 510, muscle belly portion 520, and insertion portion 530, which are located at mutually different positions. For example, when a hamstring is equally divided into three parts along the stretching direction (the extending direction) of the hamstring, origin portion 510, muscle belly portion 520, and insertion portion 530 are located in this order from the side of the gluteus maximus toward the knee. Vibration devices 110 give vibration stimulation to at least one of muscle belly portion 520 or insertion portion 530, that is, give vibration stimulation to a hamstring at a position in the two-thirds of the hamstring closer to the side of the knee.

Vibration devices 110 give vibration stimulation to at least one of muscle belly portion 520 or insertion portion 530 of one or each of the hamstrings of user 500 sitting on seat 300 by, for example, vibrating in a vibration direction (the direction parallel to the Z-axis direction according to the present embodiment) that is parallel to the direction orthogonal to the stretching direction of the hamstrings (as illustrated in FIG. 4, the stretching direction is the direction parallel to the Y-axis, according to the present embodiment). The vibration direction of vibration devices 110 is, for example, the direction orthogonal to seating surface 310. For example, in a case where seating surface 310 of seat 300 lies in a plane parallel to the horizontal direction, vibration devices 110 each vibrate in the vertical direction. In other words, in this case, the vibration direction of each vibration device 110 is the vertical direction. To rephrase, vibration devices 110 are disposed in seat 300 such that their vibration direction extends in the vertical direction. A vertically downward force is constantly applied to the body of user 500 due to the gravitational force. When vibration stimulation in the vertical direction is given to user 500, the vibration direction coincides with the direction of the force that acts on the body of user 500. This configuration makes it possible to give vibration stimulation efficiently to at least one of muscle belly portion 520 or insertion portion 530 of user 500 while the body of user 500 remains in contact with seat 300 with an appropriate pressure.

In order to activate the supplementary motor area, the muscle spindles of the hamstrings need to be activated. The muscle spindles become activated as the muscle fibers of the hamstrings are stretched. Therefore, when vibration devices 110 vibrate in the direction perpendicular to the stretching direction of the hamstrings (specifically, the extending direction of the muscle fibers of the hamstrings) to give vibration stimulation to the hamstrings, the muscle spindles can be activated effectively. For example, if the muscle fibers are seen as a string, the string can be stretched more effectively when the string is pulled in the direction orthogonal to the extending direction of the string than when the string is pulled in the extending direction of the string. Hence, the string can be made to vibrate effectively. In other words, when vibration stimulation is given to the muscle fibers in the direction orthogonal to the extending direction of the muscle fibers, the vibration stimulation can be transmitted to the muscle spindles effectively and noninvasively (i.e., the vibration stimulation can be given not directly to the muscle spindles but to the muscle spindles via the skin surface).

It is to be noted that there is no particular limitation on the cycle of vibrations of each vibration device 110. This cycle of vibrations is, for example, from 40 Hz to 120 Hz. The cycle of vibrations may be from 60 Hz to 70 Hz. With such a cycle of vibrations, vibration devices 110 can awaken user 500 more effectively (e.g., more clearly).

Vibration devices 110 each include, for example, eccentric motor 111 for generating vibrations, housing 114, projection portion 115, and leaf spring 116.

Eccentric motor 111 is a motor for generating vibrations. For example, eccentric motor 111 is electrically connected to a power source (not illustrated), such as a battery, via a power source cord or the like. Eccentric motor 111 is driven as the power from the power source is supplied to eccentric motor 111. Specifically, eccentric motor 111 is fixed to housing 114 inside housing 114. Eccentric motor 111 causes housing 114 to vibrate and thus gives vibration stimulation to user 500. Eccentric motor 111 can cause housing 114 to vibrate in one direction. Therefore, eccentric motor 111 can give vibration stimulation to user 500 in the vertical direction.

In this example, vibration devices 110 may each include, in place of eccentric motor 111, a rotary motor with a cam mechanism, a voice coil motor, a linear drive motor, or a rotary motor with a crank mechanism. Any of these motors can change the vibration direction of each vibration device 110 as desired in accordance with how these motors are installed.

Housing 114 is a box that houses eccentric motor 111. There is no particular limitation on the material, the shape, and so on of housing 114. Housing 114 includes, for example, projection portion 115 projecting in the outward direction from housing 114.

Projection portion 115 is a portion of housing 114 that projects in the outward direction from housing 114. The presence of projection portion 115 on housing 114 enables vibration devices 110 to give vibration stimulation appropriately to a specific area on user 500 (at least one of muscle belly portion 520 or insertion portion 530 of user 500). Each housing 114 is fixed to seat 300 via leaf spring 116, for example.

In this example, there is no particular limitation on the size of each projection portion 115. The size of each projection portion 115 is, for example, from 78 mm$^2$ (corresponding to $\varphi 10$ mm) to 7,854 mm$^2$ (corresponding to $\varphi 100$ mm) in terms of the area of projection portion 115 along a plane perpendicular to the vibration direction of vibration devices 110.

Moreover, there is no particular limitation on the shape of each projection portion 115. Each projection portion 115 may have a shape with a corner or a round shape, for example. Projection portion 115 may have a shape of a cylindroid, a shape of a circular column, a shape of a chamfered cylindroid or a chamfered circular column, or a shape of a dome. When projection portion 115 has any of such shapes, as compared with a case where projection portion 115 has a corner, for example, user 500 can be kept from feeling discomfort as projection portion 115 is pressed against user 500 with the stress concentrated at a very small area on user 500 where user 500 is pressed by projection portion 115.

Leaf spring 116 is a flat spring connecting housing 114 to seat 300. For example, one end of leaf spring 116 is connected to housing 114, and the other end that is the end opposite to the one end is connected to seat 300. Leaf spring 116 is disposed such that the direction normal to leaf spring 116 extends parallel to the vibration direction of housing 114, for example. With this configuration, housing 114 connected to leaf spring 116 vibrates in the direction parallel to the direction normal to leaf spring 116.

Control device 120 is a device that, by controlling vibration devices 110, causes vibration devices 110 to give vibration stimulation to at least one of muscle belly portion 520 or insertion portion 530.

Control device 120 includes, for example, a communication interface for transmitting or receiving a signal to or from each vibration device 110 or receiving device 130, a memory such as a flash memory or a hard disk drive (HDD) storing a control program, and a central processing unit (CPU) that executes the control program.

Receiving device 130 is a device that receives an instruction from user 500. Specifically, receiving device 130 receives, from user 500, an instruction that causes control device 120 to perform at least one of starting or stopping control of causing vibration devices 110 to give vibration stimulation. There is no particular limitation on receiving device 130 as long as receiving device 130 can detect a predetermined operation of user 500 indicating an instruction that causes control device 120 to perform at least one of starting or stopping control of driving vibration devices 110. Receiving device 130 is, for example but not limited to, a mechanical switch such as a push button that user 500 can depress or a sensor that detects a foot of user 500 placed on footrest 140. Receiving device 130 may be a mechanical locker switch that is disposed on footrest 140 and that user 500 can switch on or off based on the angle at which user 500 steps on the locker switch (i.e., user 500 can provide an instruction indicating whether vibration devices 110 should start or stop vibrating). Alternatively, receiving device 130 may be a mechanical button switch that can be switched on or off based on how far the switch is depressed. Based on the instruction that receiving device 130 has received, control device 120 performs at least one of starting or stopping control of causing vibration devices 110 to give vibration stimulation.

According to the present embodiment, receiving device 130 is disposed in or on footrest 140.

Footrest 140 is a support on which user 500 places at least one foot. Footrest 140 is disposed at a position where, when user 500 sitting on seat 300 has placed a foot or feet on footrest 140, at least one of muscle belly portion 520 or insertion portion 530 is in contact with seat 300 (seating surface 310 of seat 300, to be more specific). For example, marker portions 141 are provided on footrest 140 so as to indicate the positions where user 500 should place his or her feet. As long as user 500 can recognize marker portions 141, marker portions 141 may be marked on footrest 140 by being colored in a color different from the color of the rest of footrest 140 or marked in footrest 140 by a distinguishing shape, such as a concave shape or a convex shape, formed in footrest 140.

[Processing Procedure]

Next, processing procedures of awakening inducing system 200 according to Embodiment 1 will be described.

Figure 6:
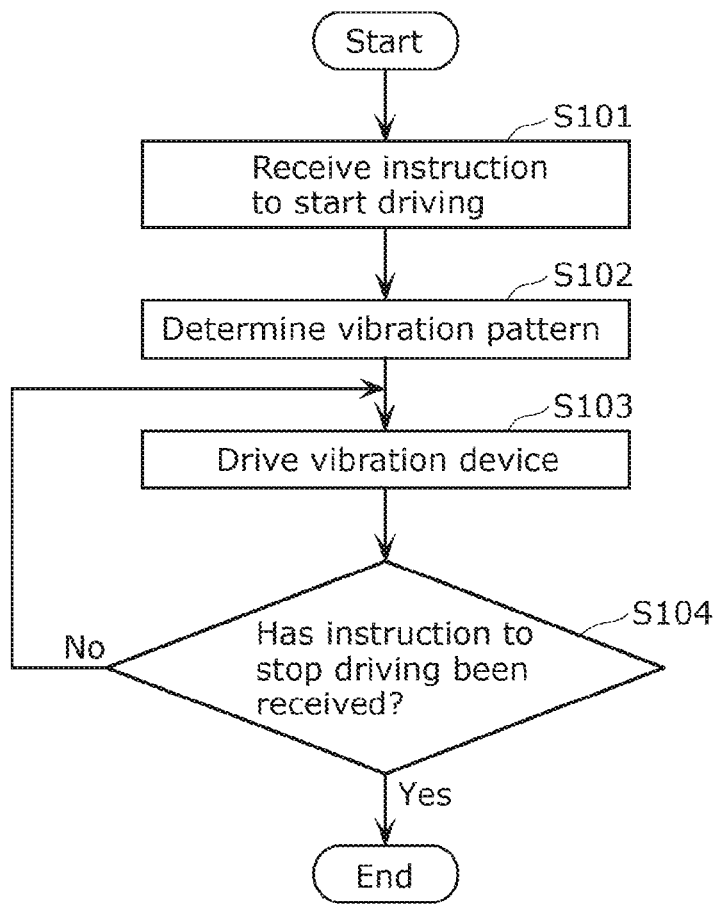
FIG. 6 is a flowchart for describing a process executed by the awakening inducing system according to Embodiment 1.

FIG. 6 is a flowchart for describing a process executed by awakening inducing system 200 (specifically, awakening inducing devices 100) according to Embodiment 1.

First, receiving device 130 receives an instruction from user 500 that causes vibration devices 110 to start being driven (i.e., causes vibration devices 110 to start vibrating) (step S101). For example, in a case where receiving device 130 is a push button, user 500 has depressed the push button.

Next, control device 120 determines a stimulation pattern of vibration stimulation to be given to user 500 (step S102). Determining a stimulation pattern includes, for example, determining the cycle of vibrations, the amplitude of vibrations, or the position on user 500 to be stimulated. For example, if user 500 is on a task, such vibration stimulation that does not startle user 500 may be given to user 500. Specific examples of a vibration pattern that is less likely to startle user 500 includes (i) a vibration pattern in which the amplitude of vibrations of each vibration device 110 is increased gradually, (ii) a vibration pattern in which the cycle of vibrations of each vibration device 110 is increased gradually, or (iii) a vibration pattern in which the intervals of vibrations of each vibration device 110 are reduced gradually (i.e., the driving frequency is increased gradually). Awakening inducing device 100 includes, for example, an operator (not illustrated), such as a keyboard or a touch panel, to be operated by user 500. Control device 120, for example, obtains information indicating a vibration pattern obtained from user 500 via the operator and determines a vibration pattern based on the obtained information.

Next, control device 120 performs control of driving vibration devices 110 such that vibration devices 110 each vibrate in the vibration pattern determined at step S102 (step S103). With this control, control device 120, by controlling vibration devices 110, causes vibration devices 110 to give vibration stimulation to at least one of muscle belly portion 520 or insertion portion 530 via seating surface 310 of seat 300.

Next, control device 120 determines whether receiving device 130 has received an instruction from user 500 that causes vibration devices 110 to stop being driven (step S104).

If control device 120 determines that receiving device 130 has received an instruction from user 500 that causes vibration devices 110 to stop being driven (Yes at step S104), control device 120 causes vibration devices 110 to stop being driven and terminates the process. For example, in a case where receiving device 130 is a push button, control device 120 causes vibration devices 110 to stop being driven and terminates the process in response to user 500 depressing the push button the second time.

Meanwhile, if control device 120 determines that receiving device 130 has not received any instruction from user 500 that causes vibration devices 110 to stop being driven (No at step S104), control device 120 returns the process to step S103.

In this example, control device 120 may stop vibration devices 110 and terminate the process after vibration devices 110 have been driven for a predetermined time set in advance. In this case, control device 120 may include a timer, such as a real time clock (RTC), for measuring the time. Such a configuration can help prevent a situation in which the effectiveness of awakening inducing device 100 in awakening user 500 decreases as user 500 becomes accustomed to the vibration stimulation.

Meanwhile, continuous vibration stimulation may cause user 500 to pay constant attention to the vibration stimulation, and this may keep user 500 from concentrating on a task, such as studying. Therefore, awakening inducing device 100 may give vibration stimulation intermittently to user 500. For example, awakening inducing device 100 may give vibration stimulation to user 500 with intervals set in advance.

Advantageous Effects and Others

As described above, awakening inducing device 100 according to Embodiment 1 includes vibration devices 110 and control device 120. Vibration devices 110 are disposed in seat 300 at respective positions where vibration devices 110 oppose at least one of muscle belly portion 520 or insertion portion 530 of one or each of the hamstrings of user 500 sitting on seat 300. Control device 120, by controlling vibration devices 110, causes vibration devices 110 to give vibration stimulation to at least one of muscle belly portion 520 or insertion portion 530.

This configuration makes it possible to give vibration stimulation to at least one of muscle belly portion 520 or insertion portion 530 of user 500.

Figure 7:
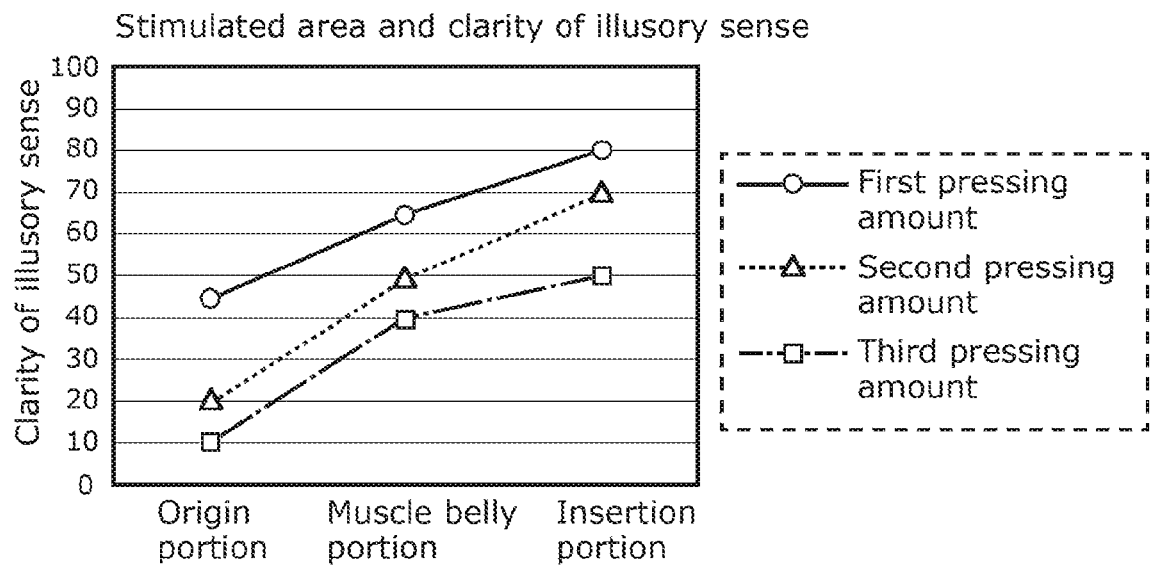
FIG. 7 is a graph for describing an effect of the awakening inducing system according to Embodiment 1.

FIG. 7 is a graph for describing advantageous effects of awakening inducing system 200 according to Embodiment 1.

Specifically, FIG. 7 shows the clarity of illusory sense reported by subjects in an experiment in which the subjects were given vibration stimulation at each of the areas of their hamstrings. In FIG. 7, the vertical axis represents the clarity of illusory sense, where 0 was assigned when no illusory sense was elicited and 100 was assigned when a very clear illusory sense was elicited. Values representing the clarity of illusory sense were obtained through self-reporting of the subjects, where the subjects reported the corresponding clarity along the continuous index axis. The vibration stimulation given to each area had a vibration frequency of 70 Hz and was given continuously for 10 seconds. The pressing amount is the amount that indicates how far each area to which vibration device 110 gave vibration stimulation was pressed. A first pressing amount was 1.8 cm, a second pressing amount was 1.3 cm, and a third pressing amount was 0.8 cm. Vibration devices 110 vibrated while being pressed into the body by any of the aforementioned pressing amounts. The vibration frequency is 70 Hz in this description, but this is not a limiting example. The vibration stimulation may have a lower frequency (e.g., lower than 70 Hz).

As illustrated in FIG. 7, a motion illusion is produced more clearly in muscle belly portion 520 or insertion portion 530 of the hamstrings than in origin portion 510. In other words, FIG. 7 shows that vibration stimulation has a high illusory effect when given to muscle belly portion 520 or insertion portion 530 of the hamstrings. Based on the above, the inventors of the present application have found that it is possible to awaken a user more fully than conventional techniques by giving vibration stimulation to at least one of muscle belly portion 520 or insertion portion 530 of user 500. In other words, awakening inducing device 100 can awaken user 500 more fully than conventional techniques by giving vibration stimulation to at least one of muscle belly portion 520 or insertion portion 530 of user 500.

For example, vibration device 110 is disposed in seat 300 at a position where vibration device 110 opposes insertion portion 530. In this case, control device 120 causes vibration device 110 to give vibration stimulation to insertion portion 530, for example.

This configuration makes it possible to give vibration stimulation to insertion portion 530 of the user. The inventors of the present application have found that it is possible to awaken user 500 more effectively by giving vibration stimulation particularly to insertion portion 530, out of muscle belly portion 520 and insertion portion 530, of user 500, as illustrated in FIG. 7. In other words, such a configuration makes it possible to awaken user 500 more effectively by giving vibration stimulation to insertion portion 530 of user 500.

For example, awakening inducing device 100 further includes footrest 140 on which user 500 places at least one foot. In this case, footrest 140 is disposed at a position where, when user 500 sitting on seat 300 has placed a foot on footrest 140, at least one of muscle belly portion 520 or insertion portion 530 is in contact with seat 300.

With this configuration, when footrest 140 is disposed at an appropriate position and when user 500 has placed one or both of his or her feet on footrest 140, user 500 can be brought into such a posture that allows vibration devices 110 to give vibration stimulation appropriately to at least one of muscle belly portion 520 or insertion portion 530. Hence, this configuration makes it possible to give vibration stimulation appropriately to at least one of muscle belly portion 520 or insertion portion 530 of user 500.

For example, awakening inducing device 100 further includes receiving device 130 that receives an instruction. In this case, receiving device 130 is disposed in or on footrest 140. For example, based on the instruction that receiving device 130 has received, control device 120 performs at least one of starting or stopping control of causing vibration devices 110 to give vibration stimulation.

This configuration can help prevent a situation in which vibration stimulation is given to user 500 at a timing that is not intended by user 500. For example, if user 500 is given vibration stimulation at a timing that is not intended by user 500 while user 500 is driving, this vibration stimulation may startle user 500, causing dangerous driving. As such, user 500 selects, via receiving device 130, the timing at which user 500 is given vibration stimulation as desired, and this can keep user 500 from being startled by vibration stimulation given at an unintended timing.

Embodiment 2

Next, a configuration of an awakening inducing system that includes an awakening inducing device according to Embodiment 2 will be described. The description of the awakening inducing system according to Embodiment 2 centers on the differences from awakening inducing system 200 according to Embodiment 1. In the description of the awakening inducing system according to Embodiment 2, configurations identical to those of awakening inducing system 200 according to Embodiment 1 are given identical reference characters, and their description will be partly simplified or omitted.

[Configuration]

Figure 8:
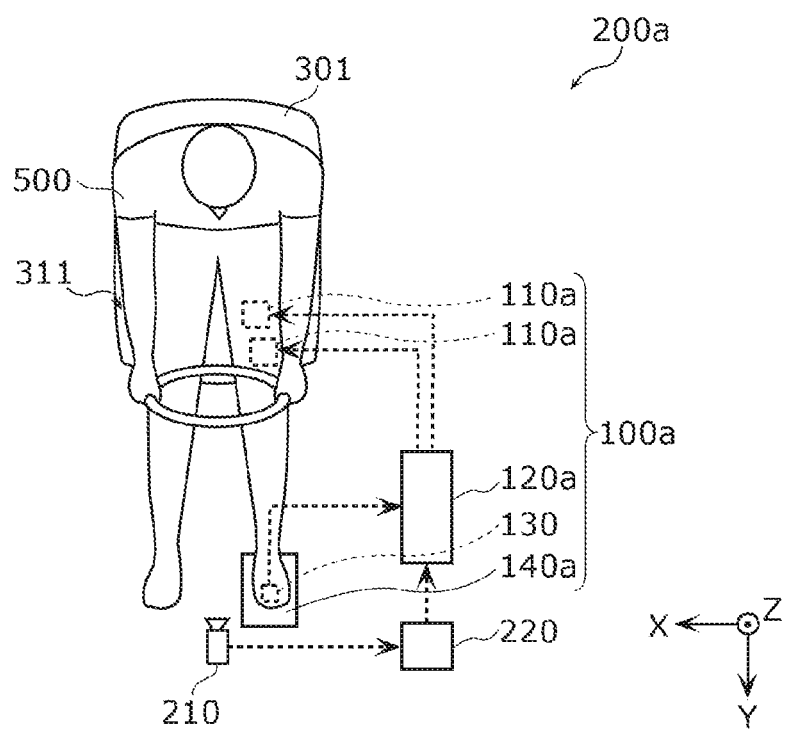
FIG. 8 is a top view illustrating an awakening inducing system according to Embodiment 2.
Figure 9:
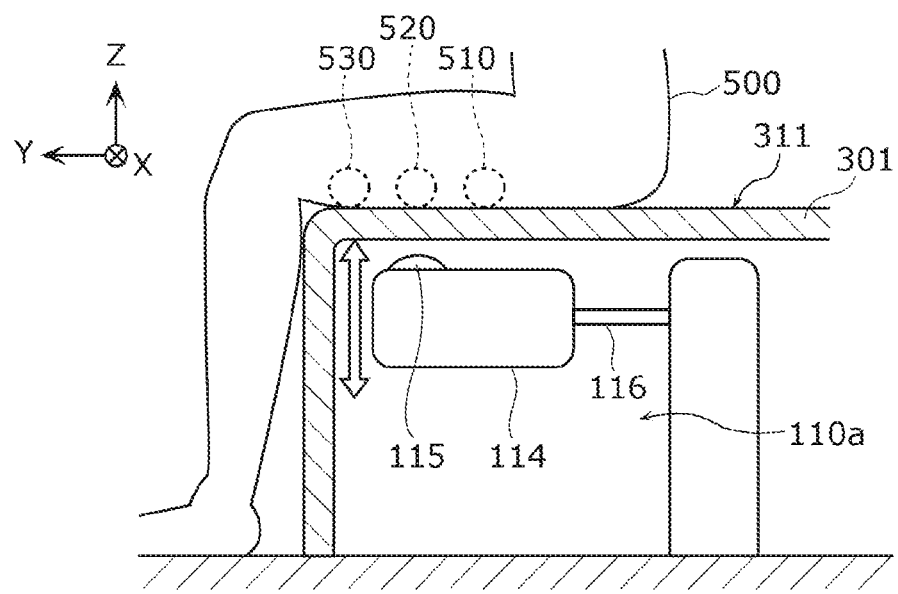
FIG. 9 is a diagram for describing a positional relationship between a vibration device according to Embodiment 2 and a user.
Figure 10:
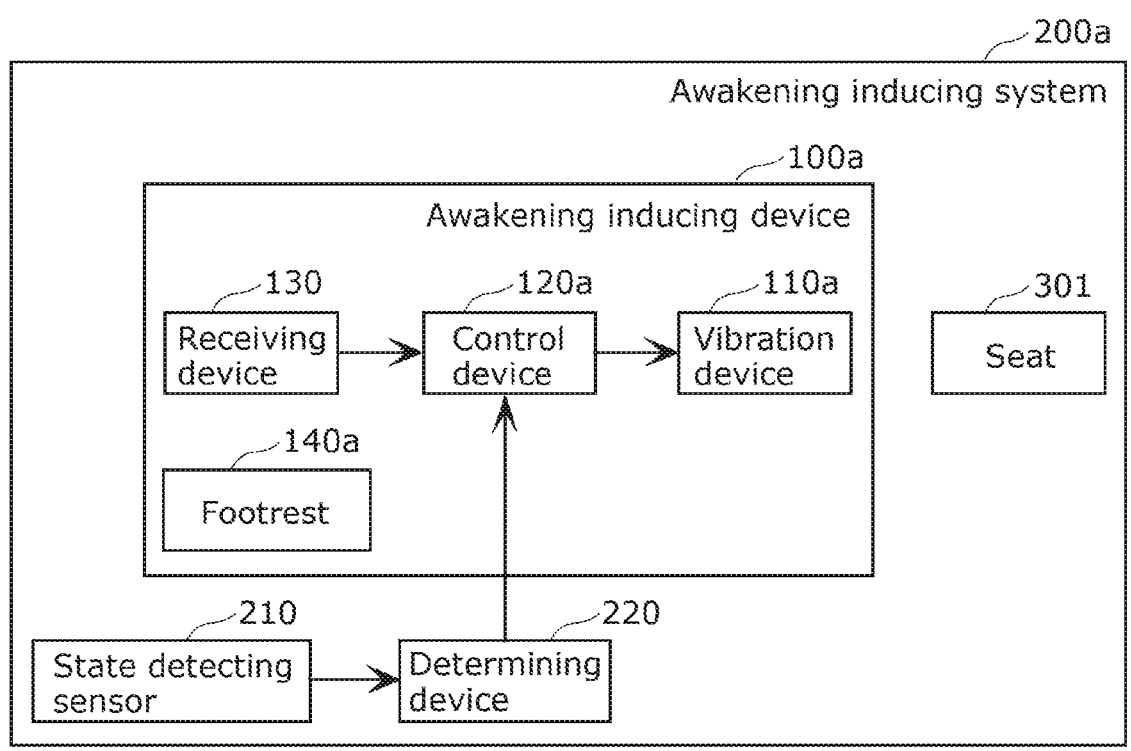
FIG. 10 is a block diagram illustrating a functional configuration of the awakening inducing system according to Embodiment 2.

FIG. 8 is a top view illustrating awakening inducing system 200a according to Embodiment 2. FIG. 9 is a diagram for describing a positional relationship between vibration device 110a according to Embodiment 2 and user 500. FIG. 10 is a block diagram illustrating a functional configuration of awakening inducing system 200a according to Embodiment 2. FIG. 8 shows two vibration devices 110a, whereas FIG. 10 shows only one vibration device 110a for description.

Awakening inducing system 200a includes awakening inducing device 100a, seat 301, state detecting sensor 210, and determining device 220.

Awakening inducing device 100a is a device that awakens user 500 by giving vibration stimulation to at least one of muscle belly portion 520 or insertion portion 530 of a hamstring of user 500 sitting in seat 301. According to the present embodiment, seat 301 is a driver's seat of a vehicle, such as an automobile. User 500 is the driver sitting in seat 301 serving as the driver's seat.

There is no particular limitation on the shape of seat 301 as long as seat 301 includes seating surface 311 on which user 500 sits. Seating surface 311 may be made of a material that can be deformed (elastically deformed) by vibration devices 110a. Seating surface 311 is formed, for example, of a cushiony material.

Awakening inducing device 100a includes vibration devices 110a, control device 120a, receiving device 130, and footrest 140a. Control device 120a is connected to each vibration device 110a and receiving device 130 such that these connected devices can transmit or receive signals therebetween via a wired circuit or a wireless circuit.

Vibration devices 110a are each a device that gives vibration stimulation to at least one of muscle belly portion 520 or insertion portion 530.

According to the present embodiment, vibration devices 110a are disposed at respective positions where vibration devices 110a oppose only the left leg of user 500 sitting in seat 301. Specifically, vibration device 110a is provided in seat 301 for the user at at least one of a position where vibration device 110a opposes muscle belly portion 520 of the hamstring of only the left leg of user 500 sitting in seat 301 or a position where vibration device 110a opposes insertion portion 530 of the hamstring of only the left leg of user 500 sitting in seat 301. In other words, each vibration device 110a is disposed in seat 301 such that vibration device 110a gives vibration stimulation to the left leg of user 500 but not to the right leg of user 500.

Vibration devices 110a give vibration stimulation to at least one of muscle belly portion 520 or insertion portion 530 of the hamstring of the left leg of user 500 sitting in seat 301 by, for example, vibrating in a vibration direction that is parallel to the direction orthogonal to the extending direction of the hamstring.

According to the present embodiment, vibration devices 110a are disposed in seat 301 between seating surface 311 and the floor surface. It suffices that vibration devices 110a each be provided in seat 301 at at least one of a position where vibration device 110a opposes muscle belly portion 520 of the hamstring of user 500 sitting in seat 301 or a position where vibration device 110a opposes insertion portion 530 of the hamstring of user 500 sitting in seat 301, and vibration devices 110a may be provided inside seat 301, under seat 301, or on top of or above seat 301. It suffices that vibration devices 110a be disposed at respective positions where vibration devices 110a can give vibration stimulation to user 500 via seating surface 311 of seat 301 in which user 500 sits.

Control device 120a is a device that, by controlling vibration devices 110a, causes vibration devices 110a to give vibration stimulation to at least one of muscle belly portion 520 or insertion portion 530 of the left leg of user 500.

Control device 120a includes, for example, a communication interface for transmitting or receiving a signal to or from each vibration device 110a or receiving device 130, a memory such as a flash memory or an HDD storing a control program, and a CPU that executes the control program.

Footrest 140a is a support on which user 500 places at least one foot. According to the present embodiment, footrest 140a is disposed at a position where user 500 places his or her left foot. Specifically, footrest 140a is disposed at a position where user 500 sitting in seat 301 places his or her left foot. In other words, footrest 140a is disposed at a position where user 500 places his or her left foot and not where user 500 places his or her right foot.

Footrest 140a is provided at a position where, when user 500 sitting in seat 301 has placed the left foot on footrest 140a, at least one of muscle belly portion 520 or insertion portion 530 is in contact with seating surface 311 of seat 301.

State detecting sensor 210 is a sensor for detecting state information that indicates a state of user 500 sitting in seat 301. Specifically, state detecting sensor 210 is a sensor for detecting the degree of drowsiness of user 500. State detecting sensor 210 is, for example, a camera.

Determining device 220 is a processing device that determines the degree of drowsiness of user 500 based on the state information detected by state detecting sensor 210. Specifically, determining device 220 calculates the degree of drowsiness of user 500.

For example, state detecting sensor 210 detects a moving image including the face of user 500 as state information. For example, determining device 220 is connected to and can communicate with state detecting sensor 210, and determining device 220 determines the degree of drowsiness of user 500 based on a moving image including user 500 captured by state detecting sensor 210.

Determining device 220 determines the degree of drowsiness of user 500 in a five point scale. For example, determining device 220 determines that the degree of drowsiness is low when user 500 blinks at regular intervals (i.e., user 500 is not drowsy) and determines that the degree of drowsiness is one. Meanwhile, determining device 220 determines that the degree of drowsiness is high when user 500 blinks slowly and frequently at short intervals (i.e., user 500 is somewhat drowsy) and determines that the degree of drowsiness is, for example, three. In other words, user 500 is determined not to be drowsy when user 500 blinks at regular intervals and determined to be drowsy when user 500 blinks slowly and frequently. In this manner, determining device 220 detects the degree of drowsiness of user 500 by analyzing a moving image including user 500 obtained from state detecting sensor 210.

In this example, the degree of drowsiness may be classified in a six or more point scale or a four or less point scale.

In one example, the user may be determined to be less drowsy as the degree of drowsiness of user 500 that determining device 220 calculates in the form of a numerical value is higher.

In the following description, the assumption is that the drowsiness is stronger as the degree of drowsiness of user 500 that determining device 220 calculates in the form of a numerical value is higher.

Determining device 220 includes, for example, a communication interface for obtaining (receiving) information that indicates the state of user 500 from state detecting sensor 210, a memory such as a flash memory or an HDD storing a control program, and a CPU that executes the control program.

In this example, control device 120a and determining device 220 may each be implemented by a separate dedicated circuit or a separate CPU or by a single dedicated circuit or a single CPU.

There is no particular limitation on how the degree of drowsiness of user 500 is determined. For example, state detecting sensor 210 may be a sensor that detects the pressure distribution across seating surface 311 on which user 500 sits. In this case, determining device 220, for example, calculates the amount of change in the centroid position of user 500 based on the pressure distribution across seating surface 311 on which user 500 sits and determines the degree of drowsiness of user 500 based on the calculated amount of change.

In this manner, state detecting sensor 210 does not need to be a camera and may be, for example but not limited to, a pressure distribution sensor, a motion sensor, a heartbeat sensor, a pulse sensor, or a breathing sensor.

The degree of drowsiness that determining device 220 determines may be the degree of drowsiness held at a desired point in time between the past and the current time calculated based on the state information accumulated in the past and the current state information or may be the degree of drowsiness to be held at a desired point in time in the future calculated based on the state information accumulated in the past and the current state information.

[Processing Procedure]

Next, processing procedures of awakening inducing system 200a according to Embodiment 2 will be described.

Figure 11:
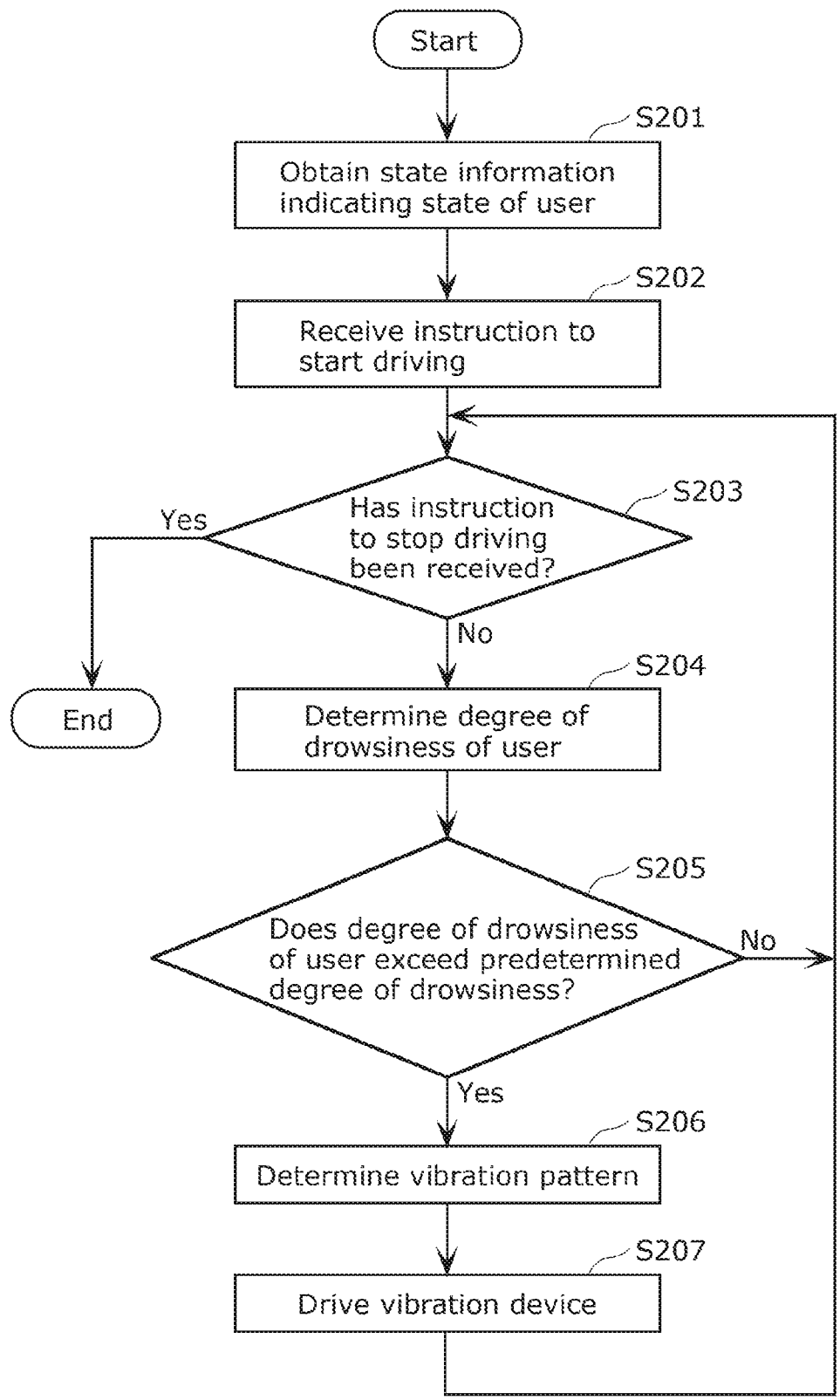
FIG. 11 is a flowchart for describing a process executed by the awakening inducing system according to Embodiment 2.

FIG. 11 is a flowchart for describing a process executed by awakening inducing system 200a according to Embodiment 2.

First, determining device 220 obtains information indicating the state of user 500 from state detecting sensor 210 (step S201). In a case where state detecting sensor 210 is a camera, determining device 220 obtains, as information indicating the state of user 500, a moving image of user 500 from state detecting sensor 210, for example.

Next, receiving device 130 receives an instruction from user 500 (step S202). For example, in a case where receiving device 130 is a push button, user 500 has depressed the push button.

In this example, state detecting sensor 210 may keep transmitting information indicating the state of user 500 to determining device 220 at desired timings. Alternatively, state detecting sensor 210 may transmit information indicating the state of user 500 to determining device 220 in response to, for example, receiving a signal that requests information indicating the state of user 500 from determining device 220. Determining device 220 may transmit a signal that requests information indicating the state of user 500 to state detecting sensor 210 in response to receiving device 130 receiving an instruction from user 500. Determining device 220 may receive information indicating that receiving device 130 has received an instruction from user 500 from control device 120a or from receiving device 130. In other words, step S201 may be executed after step S202.

Next, control device 120a determines whether receiving device 130 has received an instruction from user 500 that causes vibration devices 110a to stop being driven (step S203).

If control device 120a determines that receiving device 130 has received an instruction from user 500 that causes vibration devices 110a to stop being driven (Yes at step S203), control device 120a causes vibration devices 110a to stop being driven and terminates the process if vibration devices 110a are being driven or simply terminates the process if vibration devices 110a are not being driven.

Meanwhile, if control device 120a determines that receiving device 130 has not received any instruction from user 500 that causes vibration devices 110a to stop being driven (No at step S203), determining device 220 determines the degree of drowsiness of user 500 based on the state information indicating the state of user 500 obtained from state detecting sensor 210 (step S204).

Next, determining device 220 determines whether the degree of drowsiness of user 500 determined at step S204 exceeds a predetermined degree of drowsiness (step S205). There is no limitation on the predetermined degree of drowsiness, and the predetermined degree of drowsiness may be set in advance as desired.

If determining device 220 determines that the degree of drowsiness of user 500 does not exceed the predetermined degree of drowsiness (No at step S205), control device 120a returns the process to step S203.

Meanwhile, if determining device 220 determines that the degree of drowsiness of user 500 exceeds the predetermined degree of drowsiness (Yes at step S205), control device 120a determines a stimulation pattern of vibration stimulation to be given to user 500 (step S206). Determining a stimulation pattern includes, for example, determining the cycle of vibrations, the amplitude of vibrations, or the position on user 500 to be stimulated. Awakening inducing device 100a includes, for example, an operator (not illustrated), such as a keyboard or a touch panel, to be operated by user 500. Control device 120a, for example, obtains information indicating a vibration pattern obtained from user 500 via the operator and determines a vibration pattern based on the obtained information. Alternatively, control device 120a may determine a vibration pattern based on the degree of drowsiness of user 500.

Next, control device 120a performs control of driving vibration devices 110a such that vibration devices 110a vibrate in the vibration pattern determined at step S206 (step S207). With this control, control device 120a, by controlling vibration devices 110a, causes vibration devices 110a to give vibration stimulation to at least one of muscle belly portion 520 or insertion portion 530 of the left leg of user 500.

In this example, control device 120a determines at step S205 whether the degree of drowsiness of user 500 exceeds the predetermined degree of drowsiness. Alternatively, control device 120a may determine at step S205 whether the degree of drowsiness of user 500 is equal to or higher than the predetermined degree of drowsiness. For example, in a case where the degree of drowsiness is expressed in a numerical value and the drowsiness of user 500 is defined to be higher as the numerical value is higher, that the degree of drowsiness of user 500 exceeds the predetermined degree of drowsiness means that the numerical value representing the degree of drowsiness of user 500 is higher that the predetermined degree of drowsiness expressed by a predetermined numerical value or that the numerical value representing the degree of drowsiness of user 500 is equal to or higher than the predetermined degree of drowsiness expressed by a predetermined numerical value.

Advantageous Effects and Others

As described above, awakening inducing device 100a according to Embodiment 2 includes vibration devices 110a and control device 120a. Vibration devices 110a are disposed in seat 301 at respective positions where vibration devices 110a oppose at least one of muscle belly portion 520 or insertion portion 530 of a hamstring of user 500 sitting in seat 301. Control device 120a, by controlling vibration devices 110a, causes vibration devices 110a to give vibration stimulation to at least one of muscle belly portion 520 or insertion portion 530. Awakening inducing device 100a further includes footrest 140a on which user 500 places at least one foot. In this case, footrest 140a is disposed at a position where, when user 500 sitting in seat 301 has placed a foot on footrest 140a, at least one of muscle belly portion 520 or insertion portion 530 is in contact with seat 301. In awakening inducing device 100a, seat 301 is the driver's seat of a vehicle. In this case, footrest 140a is disposed at a position where user 500 sitting in seat 301 places his or her left foot.

In a case where seat 301 is the driver's seat of a vehicle, vibration devices 110a are disposed at respective positions where vibration devices 110a oppose only the left leg of user 500 sitting in seat 301.

If user 500 is startled by vibration stimulation while driving or if vibration stimulation is undesirable and unpleasant to user 500, this may cause user 500 to unintentionally move the leg to which the vibration stimulation has been given. The driving action of stepping on the accelerator or the brake is often carried out with the right foot. Therefore, giving vibration stimulation to the left leg can prevent a situation in which the driving of user 500 is impeded, even if user 500 has unintentionally moved the leg to which the vibration stimulation has been given. As footrest 140a is disposed at the position where the left foot is placed, when user 500 has placed the left foot on footrest 140a, user 500 can be brought into a posture that allows vibration devices 100a to give vibration stimulation appropriately to at least one of muscle belly portion 520 or insertion portion 530 of the left leg.

Awakening inducing system 200a according to Embodiment 2 includes awakening inducing device 100a, seat 301, state detecting sensor 210 that detects state information indicating a state of user 500 sitting in seat 301, and determining device 220 that determines the degree of drowsiness of user 500 based on the state information detected by state detecting sensor 210. In this case, control device 120a controls vibration devices 110a based, for example, on the determination result of determining device 220.

With this configuration, when it is determined that user 500 needs to be awakened based on the degree of drowsiness of user 500, user 500 can be awakened appropriately by being given vibration stimulation to at least one of muscle belly portion 520 or insertion portion 530 of user 500.

Embodiment 3

Next, an awakening inducing system that includes an awakening inducing device according to Embodiment 3 will be described. The description of the awakening inducing system according to Embodiment 3 centers on the differences from awakening inducing system 200 according to Embodiment 1 or awakening inducing system 200*a* according to Embodiment 2. In the description of the awakening inducing system according to Embodiment 3, configurations identical to those of awakening inducing system 200 according to Embodiment 1 or awakening inducing system 200*a* according to Embodiment 2 are given identical reference characters, and their description will be partly simplified or omitted.

[Configuration]

Figure 12:
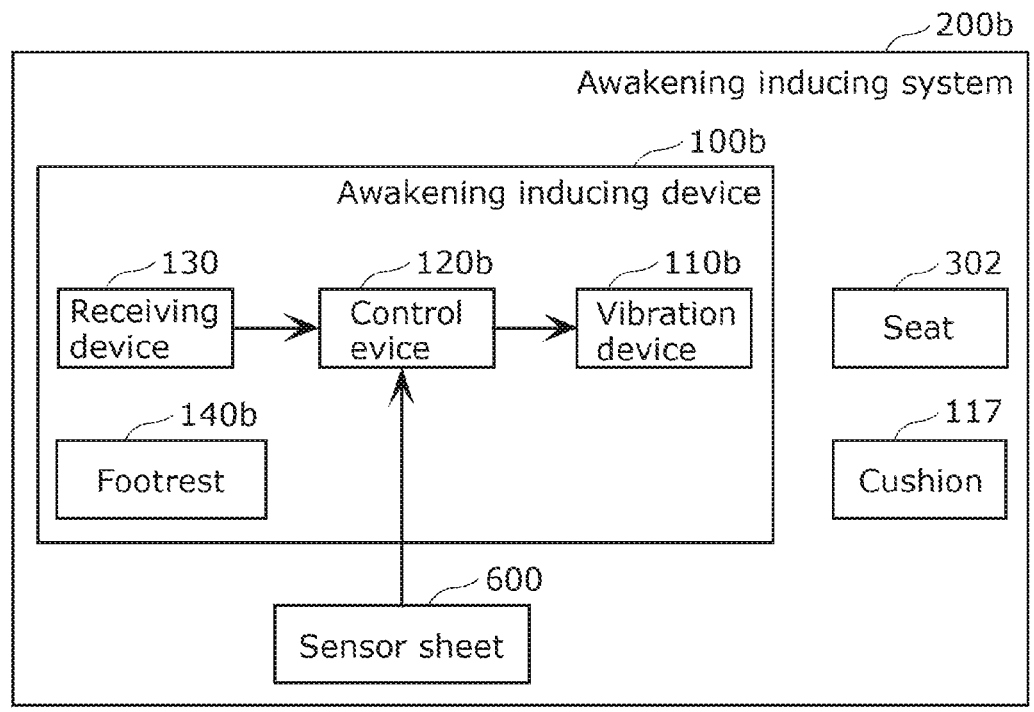
FIG. 12 is a block diagram illustrating a functional configuration of an awakening inducing system according to Embodiment 3.
Figure 13:
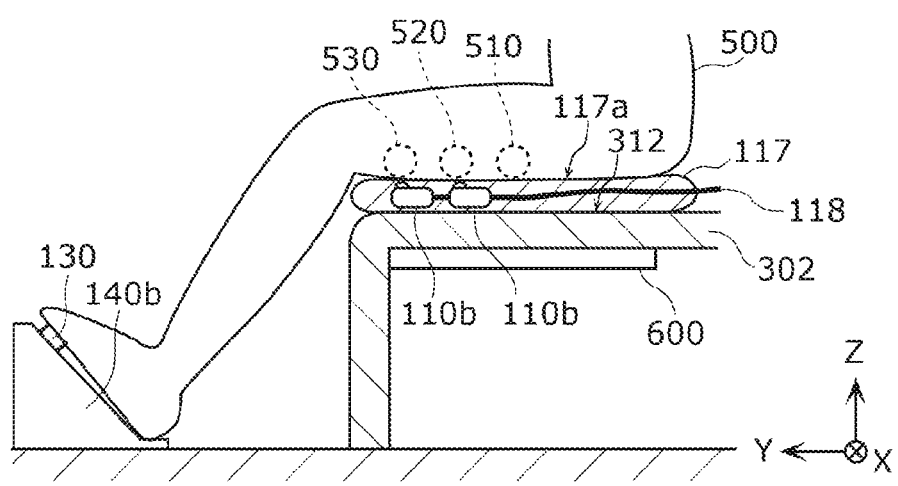
FIG. 13 is an illustration for describing a position on a user to which a vibration device according to Embodiment 3 gives vibration stimulation.
Figure 14:
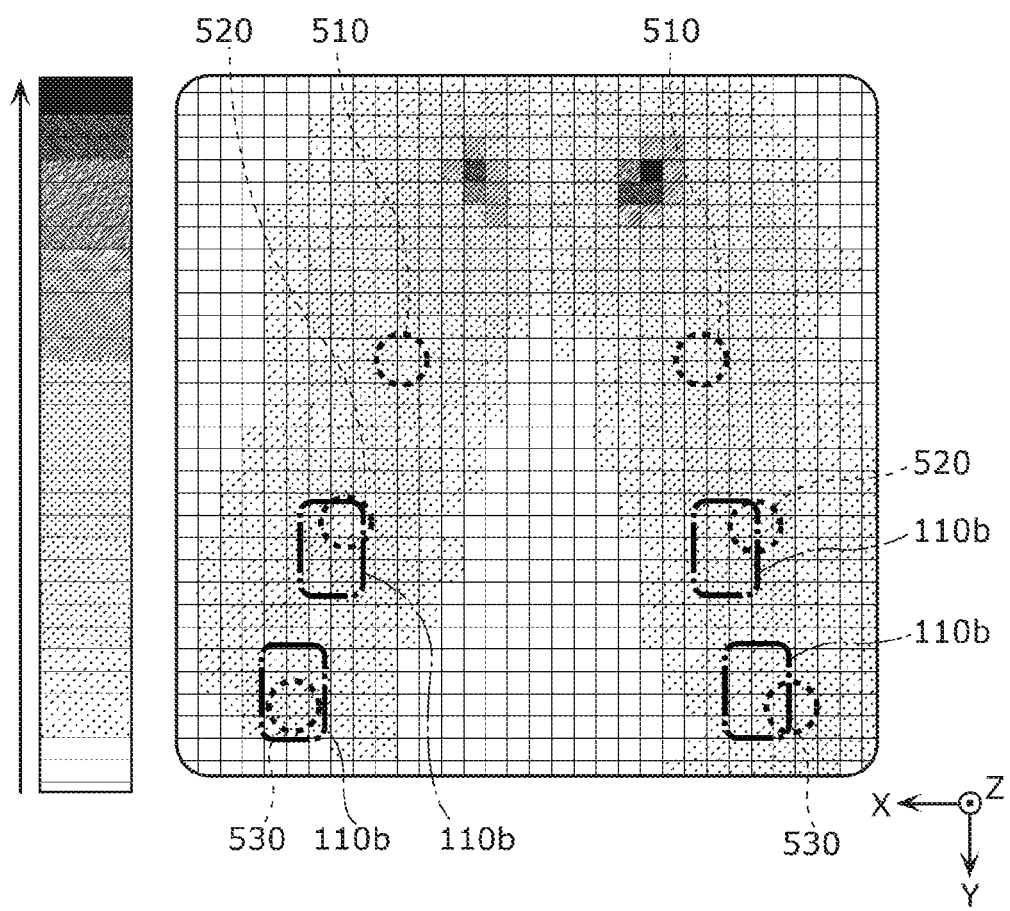
FIG. 14 is a diagram illustrating an example of a pressure distribution across a seating surface of a seat.

FIG. 12 is a block diagram illustrating a functional configuration of awakening inducing system 200*b* according to Embodiment 3. FIG. 13 is an illustration for describing positions on user 500 to which vibration devices 110*b* according to Embodiment 3 give vibration stimulation. FIG. 14 is a diagram illustrating an example of a pressure distribution across seating surface 312 of seat 302. FIG. 13 schematically illustrates the inside of cushion 117 for description. FIG. 14 shows four vibration devices 110*b*, whereas FIG. 12 shows only one vibration device 110*b* for description. FIG. 14 shows a location with a relatively higher pressure by a deeper black and a location with a relatively lower pressure by a lighter black.

Awakening inducing system 200*b* includes seat 302, cushion 117, sensor sheet 600, and awakening inducing devices 100*b*.

Awakening inducing device 100*b* are devices that awaken user 500 by giving vibration stimulation to at least one of muscle belly portion 520 or insertion portion 530 of one or each of the hamstrings of user 500 sitting on seat 302. According to the present embodiment, cushion 117 is disposed on seating surface 312 of seat 302.

Cushion 117 is, for example but not limited to, a cushion placed on seating surface 312 of seat 302 or a sheet that covers seating surface 312. According to the present embodiment, vibration devices 110*b* are disposed inside cushion 117. User 500 sits on seat 302 with cushion 117 interposed therebetween. Specifically, user 500 sits on seating surface 117*a* of cushion 117 disposed on seating surface 312 of seat 302. It suffices that vibration devices 110*b* be provided on seat 302 at at least one of a position where vibration devices 110*b* oppose muscle belly portion 520 of a hamstring of user 500 sitting on seat 302 or a position where vibration devices 110*b* oppose insertion portion 530 of a hamstring of user 500 sitting on seat 302, and vibration devices 110*b* may be provided inside seat 302, under seat 302, or on top of or above seat 302. For example, as illustrated in FIG. 13, vibration devices 110*b* may be disposed at respective positions where vibration devices 110*b* can give vibration stimulation to user 500 via seating surface 312 of seat 302 on which user 500 sits (according to the present embodiment, via seating surface 117*a* of cushion 117 placed on seating surface 312 of seat 302).

In this example, a recess portion may be formed in cushion 117 by reducing the thickness of a part of a urethane sponge or the like that cushion 117 includes for cushioning effect, and vibration devices 110*b* may be disposed in that recess portion. This configuration can reduce the likelihood that user 500 feels discomfort due to the thickness of vibration devices 110*b*.

For example, eccentric motor 111 (see FIG. 5) of each vibration device 110*b* is electrically connected to a power source (not illustrated), such as a battery, via power source cord 118 or the like and is driven as the power from the power source is supplied to eccentric motor 111.

In this example, power source cord 118 preferably extends behind (i.e., on the side of the backrest of seat 302) or on the side (e.g., the direction in which an armrest or the like of seat 302 is disposed) of user 500 so that power source cord 118 does not interfere with sitting user 500.

Sensor sheet 600 is a sensor for measuring the distribution of pressure exerted on seating surface 312 of seat 302 by user 500 sitting on seat 302. Sensor sheet 600 is disposed, for example, on the side of seat 302 opposite to the side where seating surface 312 is located. Control device 120*b* obtains pressure distribution information from sensor sheet 600, and the pressure distribution information is information that indicates the pressure distribution across seating surface 312.

Sensor sheet 600 obtains pressure distribution information that indicates a pressure distribution such as the one illustrated in FIG. 14, for example. For example, on seating surface 312, each gluteus maximus of user 500 is located at a position where the pressure is highest. The pressure decreases gradually along a relatively large distance from the position where the pressure is highest, and this gradual decrease occurs in one direction (the Y-axis direction according to the present embodiment) as compared to other directions. Each hamstring extends in this one direction from the position where the pressure is highest. Therefore, control device 120*b* can estimate the position of each hamstring of user 500 based on the pressure distribution information and can thus estimate the position of origin portion 510, muscle belly portion 520, and insertion portion 530.

In this example, it suffices that sensor sheet 600 be capable of measuring the pressure distribution, and sensor sheet 600 may detect the pressure based on the change in the resistance value or based on the change in the capacitance.

Awakening inducing device 100*b* includes vibration devices 110*b*, control device 120*b*, receiving device 130, and footrest 140*b*. Control device 120*b* is connected to each vibration device 110*b* and receiving device 130 such that these connected devices can transmit or receive signals therebetween via a wired circuit or a wireless circuit.

Vibration devices 110*b* are each a device that gives vibration stimulation to at least one of muscle belly portion 520 or insertion portion 530.

According to the present embodiment, vibration devices 110*b* are disposed inside cushion 117 so as to give vibration stimulation to seating surface 117*a* of cushion 117. For example, vibration devices 110*b* are disposed in cushion 117 such that vibration devices 110*b* do not move inside cushion 117 and can vibrate inside cushion 117. Vibration devices 110*b* are provided on seat 302 for the user at at least one of positions where vibration devices 110*b* oppose muscle belly portions 520 of the hamstrings of the legs of user 500 sitting on seat 302 or positions where vibration devices 110*b* oppose insertion portions 530 of the hamstrings of the legs of user 500 sitting on seat 302.

Vibration devices 110*b* each give vibration stimulation to at least one of muscle belly portion 520 or insertion portion 530 of one or each of the hamstrings of user 500 sitting on seat 302 via cushion 117 by, for example, vibrating in a vibration direction that is parallel to the direction orthogonal to the extending direction of the hamstrings.

Control device 120*b* is a device that, by controlling the driving of vibration devices 110*b*, causes vibration devices 110*b* to give vibration stimulation to at least one of muscle belly portion 520 or insertion portion 530 of user 500 via seating surface 117*a* of cushion 117 placed on seating surface 312 of seat 302.

Control device 120b includes, for example, a communication interface for transmitting or receiving a signal to or from each vibration device 110b, receiving device 130, or sensor sheet 600, a memory such as a flash memory or an HDD storing a control program, and a CPU that executes the control program.

Footrest 140b is a support on which user 500 places at least one foot. According to the present embodiment, footrest 140b is disposed at a position where user 500 places his or her left foot. Specifically, footrest 140b is inclined in part where footrest 140b receives a foot or the feet of user 500. There is no particular limitation on the shape of footrest 140b.

[Processing Procedure]

Next, processing procedures of awakening inducing system 200b according to Embodiment 3 will be described.

Figure 15:
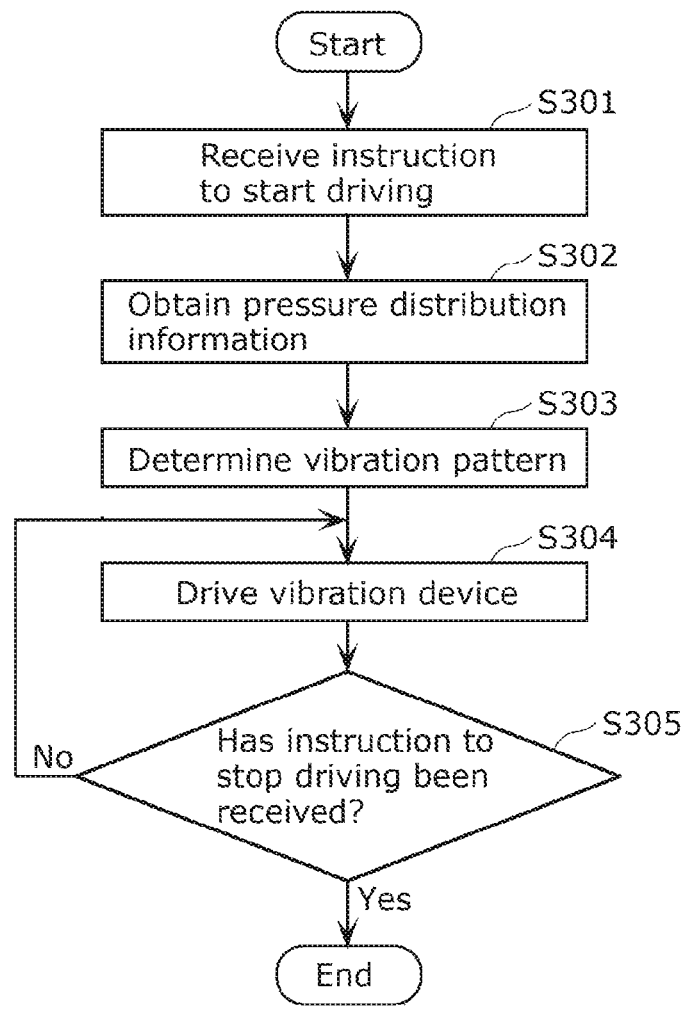
FIG. 15 is a flowchart for describing a process executed by the awakening inducing system according to Embodiment 3.

FIG. 15 is a flowchart for describing a process executed by awakening inducing system 200b according to Embodiment 3.

First, receiving device 130 receives an instruction from user 500 that causes vibration devices 110b to start being driven (step S301). For example, in a case where receiving device 130 is a push button, user 500 has depressed the push button.

Next, control device 120b, for example, obtains pressure distribution information from sensor sheet 600 (step S302).

Next, control device 120b determines a stimulation pattern of vibration stimulation to be given to user 500 (step S303). Determining this stimulation pattern includes, for example, selecting vibration device 110b to select the position on user 500 to which the vibration stimulation is to be given. For example, control device 120b selects vibration device 110b to be caused to vibrate from a plurality of vibration devices 110b based on the pressure distribution information obtained from sensor sheet 600 at step S302. For example, awakening inducing device 100b includes a plurality of vibration devices 110b each disposed at a different position. Based on the pressure distribution information obtained from sensor sheet 600 at step S302, control device 120b selects vibration device 110b that is disposed at a position where selected vibration device 110b can give vibration stimulation to at least one of muscle belly portion 520 or insertion portion 530 (e.g., vibration device 110b located at a position where vibration device 110b opposes at least one of muscle belly portion 520 or insertion portion 530). Information that indicates the position of each vibration device 110b may be stored in advance in a memory of control device 120b.

Next, control device 120b performs control of driving vibration devices 110b such that vibration devices 110b vibrate in the vibration pattern determined at step S303 (step S304). With this control, control device 120b, by controlling vibration devices 110b, causes vibration devices 110b to give vibration stimulation to at least one of muscle belly portion 520 or insertion portion 530.

Next, control device 120b determines whether receiving device 130 has received an instruction from user 500 that causes vibration devices 110b to stop being driven (step S305).

If control device 120b determines that receiving device 130 has received an instruction from user 500 that causes vibration devices 110b to stop being driven (Yes at step S305), control device 120b causes vibration devices 110b to stop being driven and terminates the process.

Meanwhile, if control device 120b determines that receiving device 130 has not received any instruction from user 500 that causes vibration devices 110b to stop being driven (No at step S305), control device 120b returns the process to step S304.

As described above, for example, control device 120b selects and drives vibration device 110b, among a plurality of vibration devices 110b, that can give vibration stimulation to at least one of muscle belly portion 520 or insertion portion 530 of user 500 based on the pressure distribution information obtained from sensor sheet 600. For example, the awakening inducing device may include a mover for changing the position of each vibration device 110b. The mover includes, for example but not limited to, a motor and a guide for moving vibration device 110b. In this case, the control device may move vibration device 110b and then drive moved vibration device 110b (cause moved vibration device 110b to vibrate) based on the pressure distribution information obtained from sensor sheet 600. This configuration allows the awakening inducing device to move vibration device 110b to an appropriate position and then give vibration stimulation to at least one of muscle belly portion 520 or insertion portion 530 of user 500. The position on user 500 to which vibration device 110b gives vibration stimulation is determined by the relative positional relationship between seating surface 312 (seating surface 117a according to the present embodiment) and vibration device 110b if the position where user 500 sits remains unchanged. Therefore, for example, awakening inducing device 100b may include a mover, such as a motor, that can change the position of seating surface 312 (or seating surface 117a) relative to vibration device 110b. Control device 120b may change the position of seating surface 312 (or seating surface 117a) by controlling the mover based on the pressure distribution information and change the position on user 500 to which vibration stimulation is given.

Awakening inducing device 100b may further include a presenter that includes, for example but not limited to, a display for displaying an image or an audio device, such as an amplifier or a speaker, for providing an audible output. Control device 120b may determine whether the position on user 500 to which vibration stimulation is to be given is appropriate based on the pressure distribution information and prompt user 500 to sit at an appropriate position by controlling the presenter based on the determination result. For example, in a case where the presenter is an audio device, control device 120b may prompt user 500 to sit at an appropriate position by causing the audio device to provide an audible output stating, for example, "please sit deeper in the seat". Alternatively, in a case where the presenter is a display, control device 120b may prompt user 500 to sit at an appropriate position by displaying an image of an appropriate posture on the display.

[Variations]

[Variations of Variation Device]

Vibration devices 110 each include eccentric motor 111 in the foregoing description, but the configuration for causing the vibration devices to vibrate is not limited to eccentric motor 111.

Figure 16:
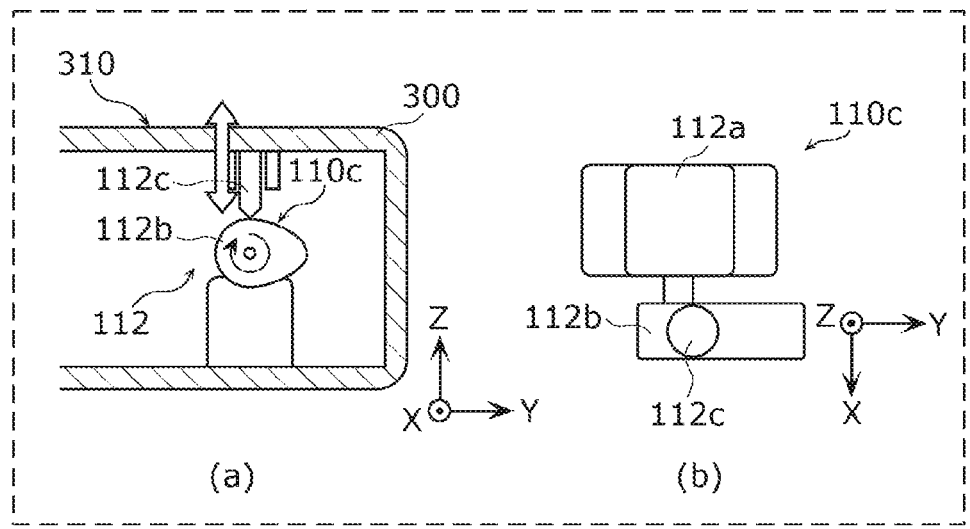
FIG. 16 is a diagram illustrating a first variation of a vibration device.

FIG. 16 is a diagram illustrating a first variation of the vibration device. Specifically, (a) in FIG. 16 is a side view illustrating the first variation of the vibration device, and (b) in FIG. 16 is a top view illustrating the first variation of the vibration device. Part (a) of FIG. 16 shows a part of the drawing in section for description.

Vibration device 110c illustrated in FIG. 16 includes rotary motor 112 with a cam mechanism, in place of eccentric motor 111.

Rotary motor 112 with a cam mechanism includes motor 112a, cam 112b, and contact element 112c.

Motor 112a is a motor that rotates cam 112b in response to the power supplied to motor 112a.

Cam 112b is a non-circular structure. Cam 112b is disposed in contact with contact element 112c.

Contact element 112c is a pin that is moved vertically by cam 112b. Vibration device 110c gives vibration stimulation to user 500 sitting on seating surface 310 by use of contact element 112c.

Figure 17:
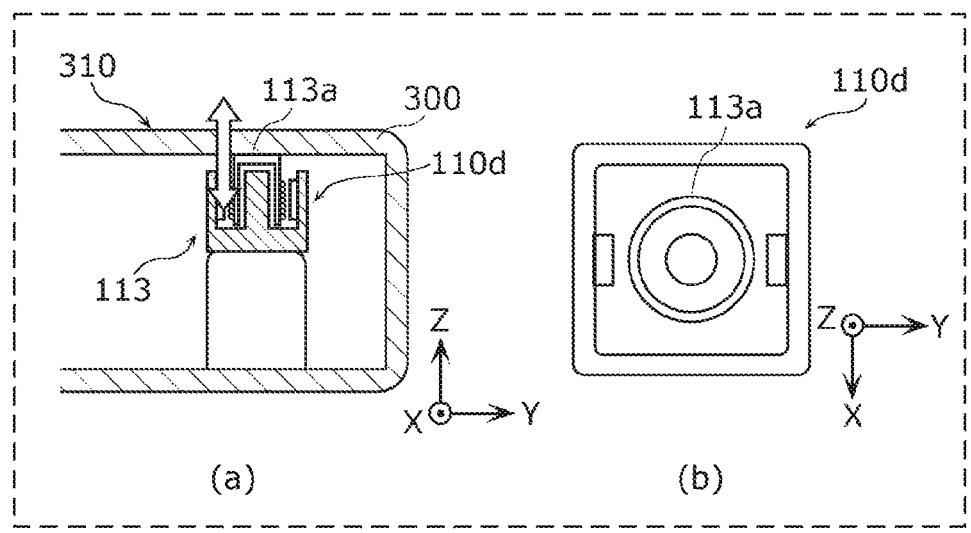
FIG. 17 is a diagram illustrating a second variation of a vibration device.

FIG. 17 is a diagram illustrating a second variation of the vibration device. Specifically, (a) in FIG. 17 is a side view illustrating the second variation of the vibration device, and (b) in FIG. 17 is a top view illustrating the second variation of the vibration device. Part (a) of FIG. 17 shows a part of the drawing in section for description.

Vibration device 110d illustrated in FIG. 17 includes voice coil motor 113.

Voice coil motor 113 causes movable element 113a to vibrate vertically by generating a magnetic field in response to the power supplied to voice coil motor 113. Vibration device 110d gives vibration stimulation to user 500 sitting on seating surface 310 by use of movable element 113a.

As described above, for example, the vibration device includes eccentric motor 111, rotary motor 112 with a cam mechanism, or voice coil motor 113. The vibration device is disposed in or on seat 300 such that the vibration direction coincides with the vertical direction, for example.

When the vibration device includes eccentric motor 111, rotary motor 112 with a cam mechanism, or voice coil motor 113, the vibration device can be made to vibrate only in one direction with a simple configuration. Therefore, such a configuration makes it possible to cause the vibration device to vibrate in the vertical direction with a simple configuration only by disposing the vibration device appropriately. A vertically downward force is constantly applied to the body of user 500 sitting on seat 300 due to the gravitational force. When vibration stimulation in the vertical direction is given to user 500, the vibration direction coincides with the direction of the force that acts on the body of user 500. This configuration makes it possible to give vibration stimulation efficiently to at least one of muscle belly portion 520 or insertion portion 530 of user 500 while the body of user 500 remains in contact with seat 300 with an appropriate pressure. Therefore, when the vibration device includes eccentric motor 111, rotary motor 112 with a cam mechanism, or voice coil motor 113 and when the vibration direction of the vibration device coincides with the vertical direction, control device 120 can cause the vibration device to give vibration stimulation to user 500 more effectively by causing the vibration device to vibrate in the vertical direction with a simple configuration.

For example, eccentric motor 111, rotary motor 112 with a cam mechanism, or voice coil motor 113 is disposed within 40 cm from the front end of seat 301. In a more specific example, vibration device 110 illustrated in FIG. 1 may be disposed within 40 cm from the front end of seat 301. In another specific example, the vibration device may include eccentric motor 111, rotary motor 112 with a cam mechanism (e.g., contact element 112c), or voice coil motor 113 (e.g., movable element 113a) provided with a projecting portion that projects like projection portion 115 illustrated in FIG. 9 and that pushes seating surface 310. In this case, the vibration device may be disposed such that the projecting portion is located within 40 cm from the front end of seat 301. The front direction in this example is the direction of sight of user 500 sitting on seat 300. In the above variations, the front direction is the positive direction along the Y-axis. The front end is the end of seat 300 in the positive direction along the Y-axis. The range of within 40 cm from the front end means, for example, the range of up to 40 cm in the back direction (in the negative direction along the Y-axis) from the front end as seat 300 is viewed from the above (when seat 300 is viewed in the Z-axis direction).

According to the anthropometric survey disclosed in Non Patent Literature 1, the linear horizontal distance from the read end of a gluteus maximus to the front end of the seating surface (a sitting gluteus maximus and a popliteal fossa distance) in a sitting posture is 59.7 cm at a maximum (approximately 60 cm). In order to present (give) vibration stimulation to at least one of the muscle belly portion or the insertion portion, the vibration stimulation may be presented to a position within two-thirds of approximately 60 cm from the front end, that is, a position within 40 cm from the front end.

With this configuration, control device 120 can, by controlling vibration devices 110, cause vibration devices 110 to give vibration stimulation appropriately to at least one of muscle belly portion 520 or insertion portion 530.

[Variation of Arrangement of Variation Devices]

Figure 18:
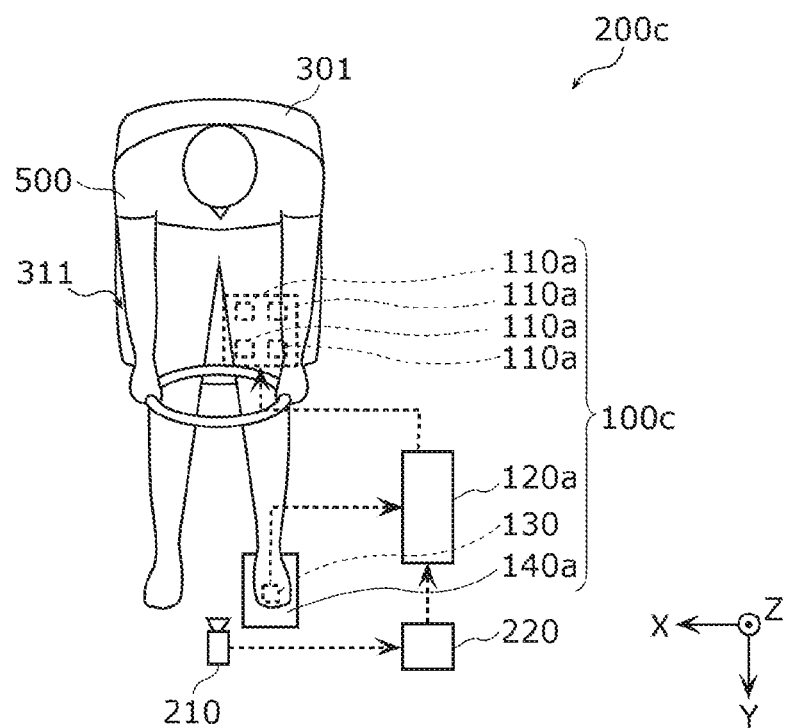
FIG. 18 is a diagram illustrating a variation in how vibration devices are arranged.

FIG. 18 is a diagram illustrating a variation in how vibration devices 110a are disposed. Awakening inducing system 200c illustrated in FIG. 18 is, for example, a variation of awakening inducing system 200a illustrated in FIG. 8 and differs from awakening inducing system 200a in terms of the number of vibration devices 110a.

Four vibration devices 110a included in awakening inducing device 100c illustrated in FIG. 18 are disposed at respective positions where vibration devices 110a oppose at least one of muscle belly portion 520 or insertion portion 530 of the left leg of user 500. In this example, four vibration devices 110a are disposed in seat 301 such that vibration devices 110a are located at positions that mutually differ in the front-back direction and the right-left direction as viewed from user 500 sitting in seat 301, for example.

For example, each vibration device 110a gives vibration stimulation only to the left leg that user 500 does not use for driving (i.e., the left leg that user 500 does not use to operate the accelerator or the brake). In this example, each vibration device 110a may be used for purposes other than the purpose of awakening user 500. For example, vibration devices 110a may be used as an attention function with the purpose of supporting user 500 in driving, and the attention function is a function of prompting user 500 to pay attention. Alternatively, vibration devices 110a may be used as an alert function for the purpose of supporting user 500 in driving, and the alert function is a function of alerting user 500 to an impending danger, for example.

The attention function is a function of, for example, presenting the direction in which user 500, the driver, is to travel in the form of vibration stimulation, by cooperating with a car navigation system (not illustrated). For example, two vibration devices 110a are disposed so as to oppose the right and left sides of insertion portion 530 of the hamstring of the left leg. When control device 120a, serving for example as a car navigation system, presents user 500 with information indicating that user 500 should turn right at the next intersection, control device 120a drives vibration device 110a located so as to oppose the right side of insertion portion 530 of the hamstring of the left leg before user 500 enters the intersection. This configuration enables user 500 to recognize, via a tactile sense, that user 500 should turn right at the next intersection.

Alternatively, control device 120a can present a warning, instead of indicating the direction of travel, by causing two vibration devices 110a disposed on the right and left sides to vibrate in an alternating manner with some time difference or by causing two vibration devices 110a disposed on the right and left sides to vibrate simultaneously. For example, awakening inducing system 200c may include a camera (not illustrated) for capturing an image of the surroundings of the vehicle driven by user 500. Control device 120a may, for example, obtain an image from the camera, determine the presence of any obstruction in the surroundings of the vehicle by analyzing the image, and drive vibration devices 110a to present a warning based on the determination result.

As described above, awakening inducing device 100c includes vibration devices 110a and control device 120a. Vibration devices 110a are provided in or on seating surface 311 of seat 301 at respective positions where vibration devices 110a oppose a gluteus maximus or a thigh portion of user 500 when user 500 serving as the driver sits in seat 301 in the vehicle and give vibration stimulation to at least one of the gluteus maximus or the thigh portion of user 500. Control device 120a controls the driving of vibration devices 110a. Vibration devices 110a are provided so as to correspond to the left leg of user 500. Control device 120a, for example, performs at least one of presenting user 500 with the traveling direction or presenting user 500 with a warning by controlling vibration devices 110a.

With this configuration, control device 120a can perform at least one of presenting user 500 with the traveling direction or presenting user 500 with a warning by controlling vibration devices 110a without interfering with the driving of user 500.

Other Embodiments

Thus far, awakening inducing devices and awakening inducing systems according to the present disclosure have been described based on some embodiments and variations, but the present disclosure is not limited to the embodiments and the variations described above. For example, an embodiment obtained by making various modifications that a person skilled in the art can conceive of to the foregoing embodiments and variations or an embodiment achieved by combining, as desired, the constituent elements and the functions in the foregoing embodiments within the scope that does not depart from the spirit of the present disclosure is also encompassed by the present disclosure.

For example, according to the foregoing embodiments, an awakening inducing system includes a state detecting sensor, a determining device, and so on. Alternatively, an awakening inducing device may include a state detecting sensor, a determining device, and so on. In this manner, the constituent elements of the awakening inducing devices or the awakening inducing systems described above are merely examples and do not limit the present disclosure.

For example, constituent elements of a processor in a control device, a determining device, or the like may be constituted by one or more electronic circuits. The one or more electronic circuits may each be a general purpose circuit or a dedicated circuit. The one or more electronic circuits may include a semiconductor device, an integrated circuit (IC), or a large scale integration (LSI) circuit, for example. An IC or an LSI circuit may be integrated into a single chip or into a plurality of chips. Although the term used herein is IC or LSI circuit, a circuit may also be called a system LSI circuit, a very large scale integration (VLSI) circuit, or an ultra large scale integration (ULSI) circuit depending on the degree of integration. A field programmable gate array (FPGA) that can be programmed after manufacturing an LSI circuit can also be used for the same purpose.

General or specific aspects of the present disclosure may be implemented in the form of a system, a device, a method, an integrated circuit, or a computer program. Alternatively, the general and specific aspects may be implemented in the form of a computer readable non-transitory recording medium, such as an optical disc, an HDD, or a semiconductor memory, storing the computer program. Furthermore, the general or specific aspects may be implemented through a desired combination of a system, a device, a method, an integrated circuit, a computer program, and a recording medium.

INDUSTRIAL APPLICABILITY

The present disclosure can be used in, for example but not limited to, a device that awakens a user such as a driver driving a mobile body while sitting in a seat.

What is claimed is:
1. An awakening inducing device comprising:
one or more vibrators disposed in a seat at a position where the one or more vibrators oppose at least one of a muscle belly portion or an insertion portion of a hamstring of a user sitting on the seat;
a processor; and
a memory including a program that, when executed by the processor, causes the processor to perform operations, the operations including:
controlling the one or more vibrators such that the one or more vibrators give vibration stimulation to the at least one of the muscle belly portion or the insertion portion, wherein
the one or more vibrators includes an eccentric motor, a rotary motor with a cam mechanism, or a voice coil motor,
the one or more vibrators includes a housing that houses the eccentric motor, the rotary motor with the cam mechanism, or the voice coil motor, and
the housing includes a projection portion projecting from the housing, the housing being configured to vibrate such that the projection portion presses the user to give the vibration stimulation to the at least one of the muscle belly portion or the insertion portion, and
the one or more vibrators vibrate in any one of:
(i) a vibration pattern in which an amplitude of vibrations of each of the one or more vibrators is increased gradually,
(ii) a vibration pattern in which a cycle of vibrations of each of the one or more vibrators is increased gradually, or
(iii) a vibration pattern in which intervals of vibrations of each of the one or more vibrators are reduced gradually.
2. The awakening inducing device according to claim 1, wherein
the one or more vibrators is disposed in the seat at a position that opposes the insertion portion, and
the processor operations include causing the one or more vibrators to give the vibration stimulation to the insertion portion.
3. The awakening inducing device according to claim 1, further comprising:
a footrest disposable at a position spaced from the seat and configured to detect input from at least one foot of the user to permit vibration stimulation of the least one of the muscle belly portion or the insertion portion of the user seated in the seat.

4. The awakening inducing device according to claim 3, wherein the processor operations further include:
receiving an instruction from the user via the footrest,
performing at least one of starting or stopping control that causes the one or more vibrators to give the vibration stimulation, based on the received instruction.

5. The awakening inducing device according to claim 3, wherein
the seat is a driver's seat of a vehicle, and
the footrest is disposed at a position where the user sitting in the driver's seat places a left foot.

6. The awakening inducing device according to claim 1, wherein
the seat is a driver's seat of a vehicle, and
the one or more vibrators is disposed at a position where the one or more vibrators opposes, of two legs of the user, only a left leg of the user sitting in the driver's seat.

7. The awakening inducing device according to claim 1, wherein
the one or more vibrators includes an eccentric motor, a rotary motor with a cam mechanism, or a voice coil motor, and
the one or more vibrators is disposed in the seat such that a vibration direction of the one or more vibrators extends in a vertical direction.

8. The awakening inducing device according to claim 7, wherein
the eccentric motor, the rotary motor with the cam mechanism, or the voice coil motor is disposed within 40 cm from a front end of the seat.

9. An awakening inducing system comprising:
the awakening inducing device according to claim 1; and
the seat, wherein
the processor operations further include:
detecting state information indicating a state of the user sitting on the seat; and
determining a degree of drowsiness of the user based on the detected state information, and
controlling the one or more vibrators based on a determination result from the determined degree of drowsiness.

10. The awakening inducing device according to claim 7, wherein
the one or more vibrators is fixed to the seat via a leaf spring that vibrates in the direction parallel to the direction normal to leaf spring.

11. The awakening inducing device according to claim 1, wherein
the projection portion has a shape of a cylindroid, a shape of a circular column, a shape of a chamfered cylindroid or a chamfered circular column, or a shape of a dome.

* * * * *